US008884608B2

(12) United States Patent
Neu et al.

(10) Patent No.: US 8,884,608 B2
(45) Date of Patent: Nov. 11, 2014

(54) AFM-COUPLED MICROSCALE RADIOFREQUENCY PROBE FOR MAGNETIC RESONANCE IMAGING AND SPECTROSCOPY

(71) Applicant: Purdue Research Foundation, West Lafayette, IN (US)

(72) Inventors: Corey P. Neu, West Lafayette, IN (US); Babak Ziaie, West Lafayette, IN (US); Teimour Maleki-Jafarabadi, Camarillo, CA (US); Charilaos Mousoulis, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/351,055

(22) PCT Filed: Oct. 10, 2012

(86) PCT No.: PCT/US2012/059602
§ 371 (c)(1),
(2), (4) Date: Apr. 10, 2014

(87) PCT Pub. No.: WO2013/055823
PCT Pub. Date: Apr. 18, 2013

(65) Prior Publication Data
US 2014/0237690 A1    Aug. 21, 2014

Related U.S. Application Data

(60) Provisional application No. 61/545,559, filed on Oct. 10, 2011.

(51) Int. Cl.
*G01R 33/12*    (2006.01)
*G01R 33/20*    (2006.01)
(Continued)

(52) U.S. Cl.
CPC ............ *G01R 33/4808* (2013.01); *G01Q 70/16* (2013.01); *G01Q 30/02* (2013.01)

USPC ...... 324/207.13; 324/318; 324/322; 324/655; 324/690; 324/696; 850/9; 850/29; 850/47; 850/48; 250/559.05; 250/559.06; 250/559.07

(58) Field of Classification Search
USPC ................... 324/207.13, 210, 244, 252, 300, 324/307–309, 318, 321, 322, 636, 655, 690, 324/696, 724, FOR. 112, FOR. 123; 250/559.01, 559.04, 559.05, 559.06, 250/559.07, 526; 850/1–3, 7–9, 25, 29, 32, 850/46–48, 60, 62, 63
See application file for complete search history.

(56) References Cited

U.S. PATENT DOCUMENTS 4,973,908 A * 11/1990 Bottomley et al. ........... 324/318
(Continued)

OTHER PUBLICATIONS

International Searching Authority, International Search Report, Mailed Apr. 15, 2014 (PCT/US2012/059602).
(Continued)

*Primary Examiner* — Bernard E Souw
(74) *Attorney, Agent, or Firm* — Ice Miller LLP

(57) ABSTRACT

The present disclosure is discloses the development of a new device, system, and method that combines advantages of magnetic resonance and atomic force microscopy technologies, and the utility of the new device, system, and method for a wide range of biomedical and clinical researchers. According to one aspect of the present disclosure, a device for microscale spectroscopy is disclosed. The micro-scale spectroscopy device includes a beam having a distal end, a proximal end, a top surface and a bottom surface, where the beam is attached to an anchor at the proximal end and further includes a tip extending substantially perpendicular from the bottom surface at or near the distal end, and a coil having at least one turn mounted to the top surface of the beam at or near the distal end opposite the tip, where the coil is capable of both transmitting and sensing electromagnetic radiation.

32 Claims, 20 Drawing Sheets

(51) Int. Cl.
*G01N 24/08* (2006.01)
*G01Q 70/16* (2010.01)
*G01Q 30/02* (2010.01)
*G01R 33/48* (2006.01)

(56) References Cited

U.S. PATENT DOCUMENTS

| | | | | |
|---|---|---|---|---|
| 5,619,139 | A * | 4/1997 | Holczer et al. | 324/318 |
| 6,937,020 | B2 * | 8/2005 | Munson et al. | 324/321 |
| 7,056,455 | B2 * | 6/2006 | Matyjaszewski et al. | 264/29.2 |
| 7,146,282 | B1 * | 12/2006 | van der Weide et al. | 702/56 |
| 7,626,391 | B2 * | 12/2009 | Munson et al. | 324/318 |
| 8,168,120 | B1 * | 5/2012 | Younis | 422/82.01 |
| 8,501,097 | B1 * | 8/2013 | Younis | 422/82.01 |
| 2003/0185741 | A1 * | 10/2003 | Matyjaszewski et al. | 423/445 R |
| 2004/0095133 | A1 * | 5/2004 | Nikitin et al. | 324/210 |
| 2004/0222796 | A1 * | 11/2004 | Munson et al. | 324/322 |
| 2008/0100296 | A1 * | 5/2008 | Massin et al. | 324/321 |
| 2008/0169814 | A1 * | 7/2008 | Munson et al. | 324/321 |

OTHER PUBLICATIONS

International Searching Authority, Written Opinion of the International Searching Authority, mailed Apr. 15, 2014 (PCT/US2012/059602).

* cited by examiner

AFM-COUPLED MICROSCALE RADIOFREQUENCY PROBE FOR MAGNETIC RESONANCE IMAGING AND SPECTROSCOPY

RELATED APPLICATIONS

The present application is related to, claims the priority benefit of, and is a U.S. §371 national stage entry of, International Patent Application Serial No. PCT/US2012/059602, filed Oct. 10, 2012, which is related to and claims the priority benefit of U.S. Provisional Patent Application Ser. No. 61/545,559, filed Oct. 10, 2011. The contents of each of these applications are hereby incorporated by reference in their entirety into this disclosure.

TECHNICAL FIELD

The present disclosure generally relates to imaging systems and, in particular, to atomic force microscopy (AFM) and nuclear magnetic resonance (NMR) technologies and spectroscopy.

BACKGROUND

Technologies that provide information on the single cell level may inevitably reveal specific mechanisms in a broad range of biological processes, from embryogenesis to aging. Most modern technologies study large populations of cells, with persistent heterogeneity of cells in different stages of growth or disease, yielding only an average measure of cellular function. However, studies at the single cell level are necessary to minimize inherent variability of measures from cell populations and enable detailed investigations for advanced cellular knowledge.

Information extracted from such studies is particularly useful when correlated with cell mechanics and adhesion properties. There are a variety of techniques that can elucidate these properties, for example, magnetic tweezers, optical tweezers, and atomic force microscopy (AFM). A comprehensive review illustrating the strengths and weaknesses of these techniques applied to single molecules is given by Neuman and Nagy. AFM provides a method of cellular stiffness measurement, in a non-destructive way by applying nanoscale forces to a cell. As opposed to traditional optical imaging, AFM indirectly visualizes the cell surface morphology via monitoring the deflection of a sensing cantilever. AFM can further acquire stretching curves, through the pressing of the cantilever on the surface and determining the subsequent adhesion during the tip retraction. A distinct advantage of this technology is that other techniques such as brightfield, confocal, and fluorescence microscopy can be incorporated to enable cellular shape and labeling of proteins on the cell interior.

Nuclear magnetic resonance (NMR) imaging was introduced in 1973 and has since become a primary diagnostic tool in medical science for internal tissue morphology, disease, and function. To reveal microstructures and sub microstructures of objects, considerable efforts have been made to improve the resolution of NMR microscopy to depict elements smaller than 100 cubic microns ($\mu m^3$). However, the practical constraints imposed by modern imaging systems are currently thought to limit spatial resolution to about 1.0 microns ($\mu m$) and volume elements to less than 64 $\mu m^3$. Moreover, reported spatial resolutions for cellular imaging are rather poor, around 3 $\mu m$, and the acquisition times are long (i.e., approximately 8 hours).

Accordingly, there is a need for a device and method that enables the analysis of cellular structures and local biochemistry to speed innovative basic research toward treatments and cures of cellular disease. Such a device and method would provide a foundation for the analysis of local biomechanical and chemical environments of single cells in the context of disease, potentially enabling the success of embedded individual cells used for regeneration of functional tissue engineered constructs.

SUMMARY

The present disclosure is discloses the development of a new device, system, and method that combines advantages of magnetic resonance and atomic force microscopy technologies, and the utility of the new device, system, and method for a wide range of biomedical and clinical researchers.

According to one aspect of the present disclosure, a device for micro-scale spectroscopy is disclosed. The micro-scale spectroscopy device includes a beam having a distal end, a proximal end, a top surface and a bottom surface, where the beam is attached to an anchor at the proximal end and further includes a tip extending substantially perpendicular from the bottom surface at or near the distal end, and a coil having at least one turn mounted to the top surface of the beam at or near the distal end opposite the tip, where the coil is capable of both transmitting and sensing electromagnetic radiation.

In at least one embodiment of the present disclosure, micro-scale spectroscopy device includes at least one piezoelectric element mounted to the top surface of the beam at or near the proximal end, where the at least one piezoelectric element is capable of generating a deflection signal due to strain in the beam due to a deflection of the distal end and of moving the distal end, and at least two piezo contacts are electrically connected to the at least one piezoelectric element and disposed adjacent to the anchor.

In at least one embodiment of the present disclosure, micro-scale spectroscopy device includes a tip formed integral to the beam. In at least one embodiment of the present disclosure, micro-scale spectroscopy device includes a tip that is spherically shaped. In at least one embodiment of the present disclosure, micro-scale spectroscopy device includes a coil with two ends and at least two leads electrically connected to the coil, where at least one lead is connected to each of the two ends and at least two coil contacts are electrically connected to the at least two leads and disposed adjacent the anchor.

In at least one embodiment of the present disclosure, micro-scale spectroscopy device includes a beam formed of a silicon material with a thickness of no more than approximately 2 microns, and a spring constant between approximately 0.01 and 1.0 newtons per meter. In at least one embodiment of the present disclosure, micro-scale spectroscopy device includes a probe that include a beam and a coil and is capable of identifying biophysical and biochemical characteristics of a sample contacted by the tip of the probe. In at least one embodiment of the present disclosure, micro-scale spectroscopy device includes a probe that is capable of determining a morphology of the sample. In at least one embodiment of the present disclosure, micro-scale spectroscopy device includes a probe that is capable of isolating intercellular structures within a cell contacted by the tip of the probe.

According to one aspect of the present disclosure, a system for micro-scale spectroscopy is disclosed. In at least one embodiment of the present disclosure, a system for micro-scale spectroscopy includes a probe, which includes a beam having a distal end, a proximal end, a top surface and a bottom surface, the beam being attached to an anchor at the proximal end and further including a tip extending substantially perpendicular from the bottom surface at or near the distal end, a coil having at least one turn and mounted to the top surface of the beam at or near the distal end opposite the tip, where the coil is capable of both transmitting and sensing electromagnetic radiation, at least two leads electrically connected to the coil, and at least two coil contacts electrically connected to the at least two leads and disposed adjacent to the anchor. The system further includes a spectrometer electrically connected to the at least two coil contacts, where the spectrometer is capable of transmitting electromagnetic radiation via the coil and of performing a Fourier analysis of the electromagnetic radiation sensed by the coil, and where the probe is capable of atomic force microscopy via deflection of the beam when the tip is contacted with a sample and, when positioned within a magnetic field, is capable of nuclear magnetic resonant spectroscopy by transmission to and reception of electromagnetic radiation from the sample via the coil.

In at least one embodiment of the present disclosure, a system for micro-scale spectroscopy includes a magnetic field generated by a magnet having a field strength between approximately 0 and 30 Tesla. In at least one embodiment of the present disclosure, a system for micro-scale spectroscopy includes at least one piezoelectric element mounted to the top surface of the beam at or near the proximal end, where the at least one piezoelectric element is capable of generating a deflection signal due to strain in the beam due to a deflection of the distal end and of moving the distal end, at least two piezo contacts electrically connected to the at least one piezoelectric element and disposed adjacent to the anchor, and a deflection circuit electrically connected to the at least two piezo contacts, the deflection circuit capable of receiving the deflection signal form the at least one piezoelectric element and of generating a movement in the at least one piezoelectric element. In at least one embodiment of the present disclosure, a system for micro-scale spectroscopy includes a data acquisition system electrically connected to the probe, where the data acquisition system includes a tuning circuit electrically connected to the at least two coil contacts, the tuning circuit capable of calibrating the coil and a spectrometer. In at least one embodiment of the present disclosure, a system for micro-scale spectroscopy includes a tuning circuit having a first capacitor electrically connected in parallel with the probe and a second capacitor electrically connected in series with the first capacitor and the probe.

In at least one embodiment of the present disclosure, a system for micro-scale spectroscopy includes a probe that is capable of identifying biophysical and biochemical characteristics of a sample contacted by the tip of the probe. In at least one embodiment of the present disclosure, a system for micro-scale spectroscopy includes a probe that is capable of determining a morphology of the sample. In at least one embodiment of the present disclosure, a system for micro-scale spectroscopy includes probe that is capable of isolating intercellular structures within a cell contacted by the tip of the probe.

According to one aspect of the present disclosure, a method of micro-scale spectroscopy using a AFM/NMR probe is disclosed. In at least one embodiment of the present disclosure, a method of micro-scale spectroscopy using a AFM/NMR probe includes placing a sample to be analyzed into a magnetic field, introducing a probe into proximity with the sample, where the probe includes a beam having a distal end, a proximal end, a top surface and a bottom surface, the beam being attached to an anchor at the proximal end and further includes a tip extending substantially perpendicular from the bottom surface at or near the distal end, a coil having at least one turn mounted to the top surface of the beam at or near the distal end opposite the tip, where the coil is capable of both transmitting and sensing electromagnetic radiation. A method of micro-scale spectroscopy using a AFM/NMR probe also includes moving the probe until the tip contacts a surface of the sample, thereby ensuring close proximity between the coil and the sample, scanning the surface with the tip by moving the tip across the surface of the sample, while the tip is in contact with the surface of the sample, generating an electromagnetic field via the coil, the electromagnetic field being localized to the sample, waiting a period of time for nuclei within the sample to generate a resonant signal in response to the electromagnetic field generated from the coil and acquiring the resonant signal generated by the nuclei within the sample via the coil.

In at least one embodiment of the present disclosure, a method of micro-scale spectroscopy using a AFM/NMR probe includes generating the electromagnetic field via the coil and acquiring the resonant signal generated by the nuclei at multiple locations across the surface of the sample. In at least one embodiment of the present disclosure, a method of micro-scale spectroscopy using a AFM/NMR probe includes applying a surface chemistry to the surface of the sample, the surface chemistry selected from the group consisting of fibronectin, poly-1-lysine, and collagen. In at least one embodiment of the present disclosure, a method of micro-scale spectroscopy using a AFM/NMR probe includes conducting Fourier transform spectroscopy on the resonant signal generated by the nuclei using a spectrometer. In at least one embodiment of the present disclosure, a method of micro-scale spectroscopy using a AFM/NMR probe includes a spectrometer capable of both generating an electromagnetic field generated via the coil and acquiring the resonant signal generated by the nuclei within the sample. In at least one embodiment of the present disclosure, a method of micro-scale spectroscopy using a AFM/NMR probe includes an electromagnetic field generated via the coil that includes multiple pulses of electromagnetic radiation. In at least one embodiment of the present disclosure, a method of micro-scale spectroscopy using a AFM/NMR probe includes determining a morphology of the sample. In at least one embodiment of the present disclosure, a method of micro-scale spectroscopy using a AFM/NMR probe includes determining an adhesion property of the surface of the sample. In at least one embodiment of the present disclosure, a method of micro-scale spectroscopy using a AFM/NMR probe includes determining biophysical and biochemical characteristics of a sample contacted by the tip of the probe.

According to one aspect of the present disclosure, a method of fabricating a AFM/NMR probe is disclosed. In at least one embodiment of the present disclosure, a method of fabricating a AFM/NMR probe includes providing a beam, where the beam includes a beam having a distal end, a proximal end, a top surface and a bottom surface, the beam being attached to an anchor at the proximal end and further includes a tip extending substantially perpendicular from the bottom surface at or near the distal end. In at least one embodiment of the present disclosure, a method of fabricating a AFM/NMR probe further includes applying a first insulation layer of insulating material on the top surface of the beam, applying a first conductive layer of electrically conductive material to the first insulation layer on the beam, and etching the first conductive layer to define a coil at or near the distal end opposite the tip, at least one lead adjacent the coil, and at least one contact adjacent the at least one lead at or near the proximal end, wherein the coil, at least one lead, and at least one contact are electrically connected.

In at least one embodiment of the present disclosure, a method of fabricating a AFM/NMR probe includes etching using a focused ion beam milling process. In at least one embodiment of the present disclosure, a method of fabricating a AFM/NMR probe includes applying a second insulation layer to the beam, etching the second insulation layer to form a passage to one end of the coil, applying a second conductive layer of electrically conductive material to the second insulation layer on the beam, and etching the second conductive layer to form at least one lead in electrical contact with the coil via the passage.

In at least one embodiment of the present disclosure, a method of fabricating a AFM/NMR probe includes forming a wafer having a top surface and a bottom surface with a first oxide layer thereon, etching the wafer to form an trench in the top surface, applying a second oxide layer within the trench further etching the coated opening to form a desired tip shape, depositing a structural layer to the top surface and into the trench to form a beam and a tip, where the beam defines a top surface, a bottom surface, a distal end, and a proximal end, and where the tip extends substantially perpendicular from the bottom surface at or near the distal end, depositing a first conductive layer on the top surface over the structural layer to form a coil and at least one lead adjacent the coil, wherein the coil includes one or more ends and is disposed at or near the distal end of the beam opposite the tip, and wherein the at least one lead extends to the proximal end of the beam, applying an insulation layer over the first conductive layer, etching the first insulation layer to form one or more passages to the at least one lead and one end of the coil, depositing a second conductive layer over the first insulation layer to form an electrical connection between one end of the coil and at least one lead via the one or more passages, applying a second insulation layer over the second conductive layer, applying a third oxide layer over the second insulation layer, dissolving a portion of the wafer surrounding the tip, and dissolving the second oxide layer from area surrounding the tip.

DETAILED DESCRIPTION

Figure 1:
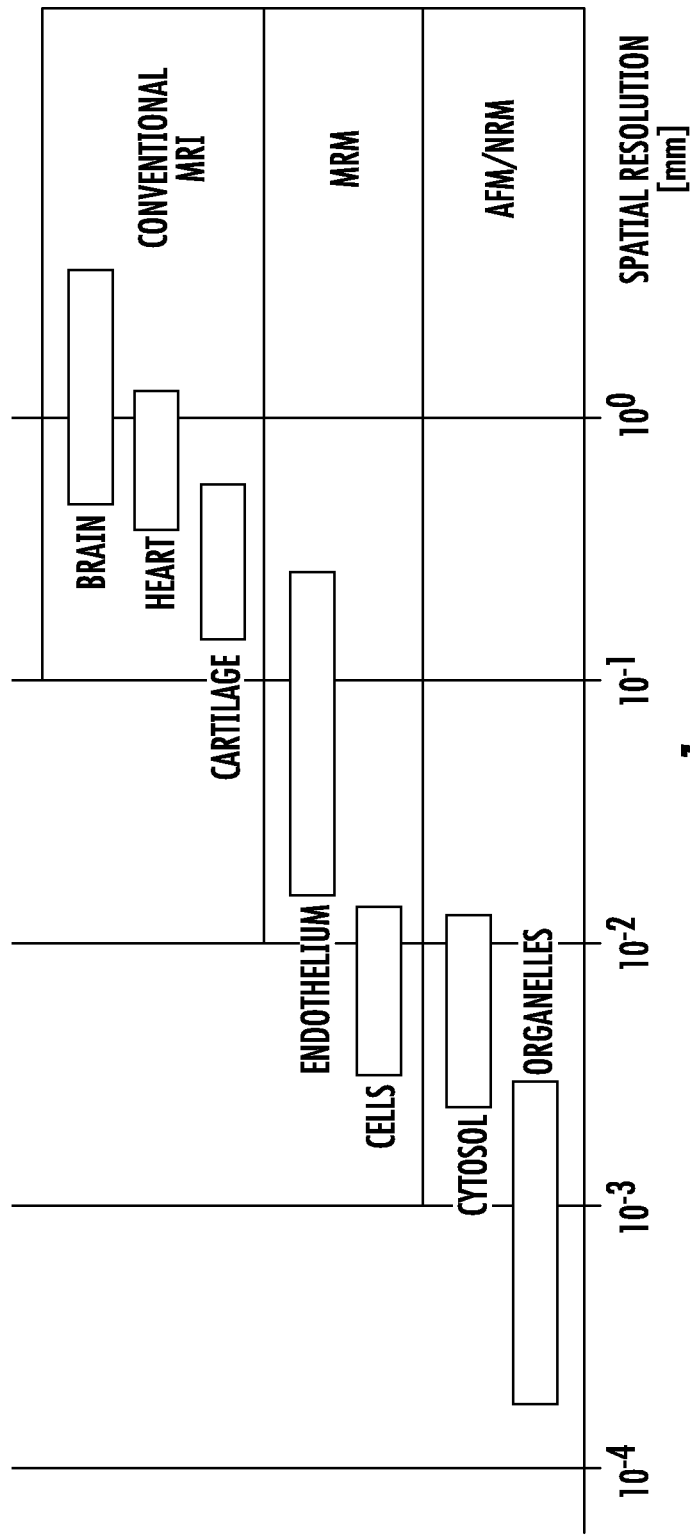
FIG. 1 is a graph depicting conventional MRM being limited in its ability to resolve cellular structures and localized spectroscopic data.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel system for real-time biophysical, chemical, and structural analysis of single cells is disclosed, which combines the atomic-scale spatial localization, mechanical, and surface analysis features of atomic force microscopy (AFM) with the localized capabilities of nuclear magnetic resonance (NMR) imaging and spectroscopy. The hybrid AFM/NMR probe of the present disclosure includes nanofabricated planar radiofrequency coils formed on a deflectable AFM sensing probe for highly-focused localized spectroscopy and nanometer discretized cell localization. The disclosed innovative combination of AFM and NMR technologies within a single device, first, enables the study of cell heterogeneity which, in cases such as cancer, can provide valuable insight and lead to more effective treatments. Second, the NMR capability facilitates identification and classification of malignant cells. Third, while the mechanical interaction of the cell with the matrix is studied by the AFM capability, the NMR capability can provide insightful intercellular chemical information. For example, matrix stiffness has been shown to influence proliferation and tumorigenesis. Therefore, the combination of AFM and NMR technologies may enable novel insights into new therapies for cellular disease.

As shown in FIG. 1, conventional magnetic resonance imaging (MRI) technology has a spatial resolution limited to approximately 100 microns (μm) and is therefore limited to the study of large populations of cells and relatively large tissue structures, for example, the brain or the heart. Magnetic resonance microscopy (MRM) has been demonstrated capable of achieving spatial resolutions of 10 enabling the study of tissue structures such as the endothelium. On the other hand, the hybrid AFM/NMR probe according to the present disclose is capable spatial resolution of at least 1 μn, which enables the study of individual cellular structures, such as organelles, within mammalian cells. Further, the hybrid AFM/NMR probe enables the optimization of the detection resolution and performance of AFM-coupled micro radiofrequency probes in the context of local spectroscopy and stiffness of single cells.

Figure 2:
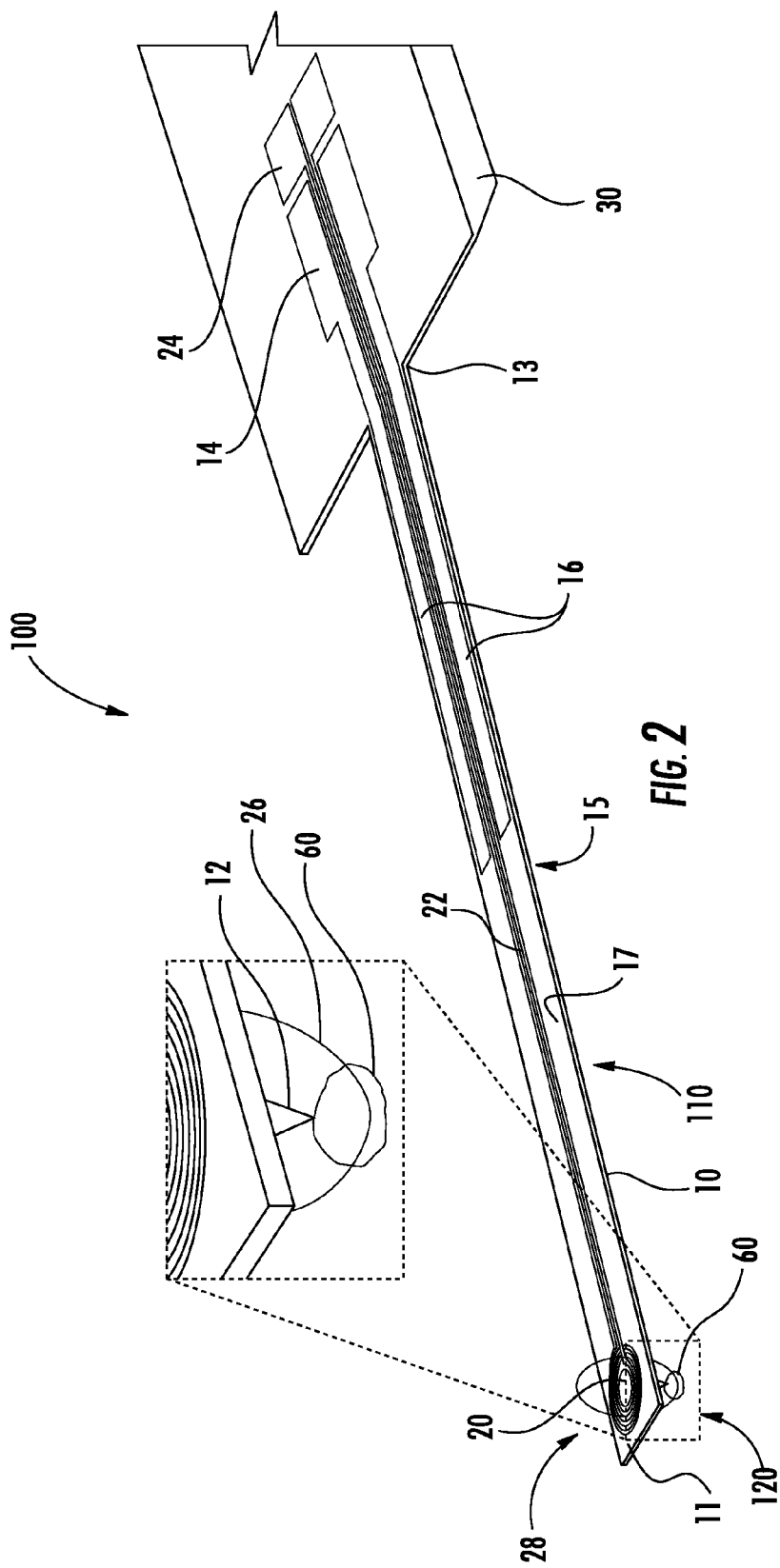
FIG. 2 shows perspective and detailed views of a AFM/NMR probe according to the present disclosure.

Shown in FIG. 2 is a hybrid AFM/NMR probe 100, according to at least one embodiment of the present disclosure. The hybrid AFM/NMR probe 100 includes an AFM subsystem 110 and a NMR subsystem 120 integrated into a single AFM/NMR probe 100. The AFM subsystem 110 may include a cantilever beam 10 mounted to an anchor 30 at a proximal end 13 and having a tip 12 formed at or near an opposite distal end 11. As shown in FIG. 2, the tip 12 may extend from a bottom surface 15 of the beam 10. In at least one embodiment, the tip 12 may extend substantially perpendicularly from the bottom surface 15. The beam 10 may further include a top surface 17, opposite the bottom surface 15, having one or more piezoelectric elements 16 attached thereto. In at least one embodiment, the beam may be formed of silicon nitride with dimensions of 600 μm×200 μm×1 μm. In at least one embodiment according to the present disclosure, the beam 10 may be up to 2 μm thick with a width between approximately 50 μm and 500 μm and a length between approximately 300 μm and 3000 μm. In at least one embodiment, the dimensions of the beam 10 may be selected such that the spring constant of the beam 10 ranges between approximately 0.01-1.0 Newtons per meter (N/m). Further, the tip 12 may be include any suitable shape that creates a distance from the bottom surface 15 of the beam 10, including without limitation cylindrical, conical, or spherical.

Figure 3:
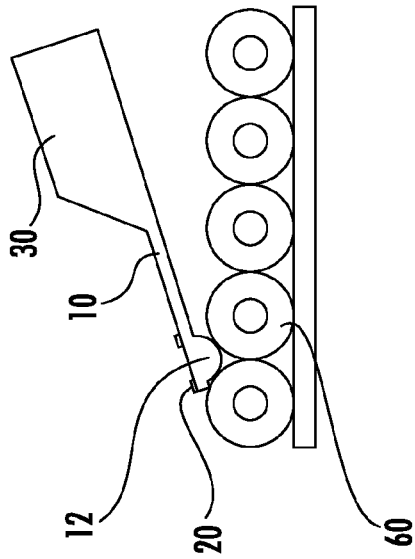
FIG. 3 depicts a method of use of a AFM/NMR probe according to the present disclosure.
Figure 4:
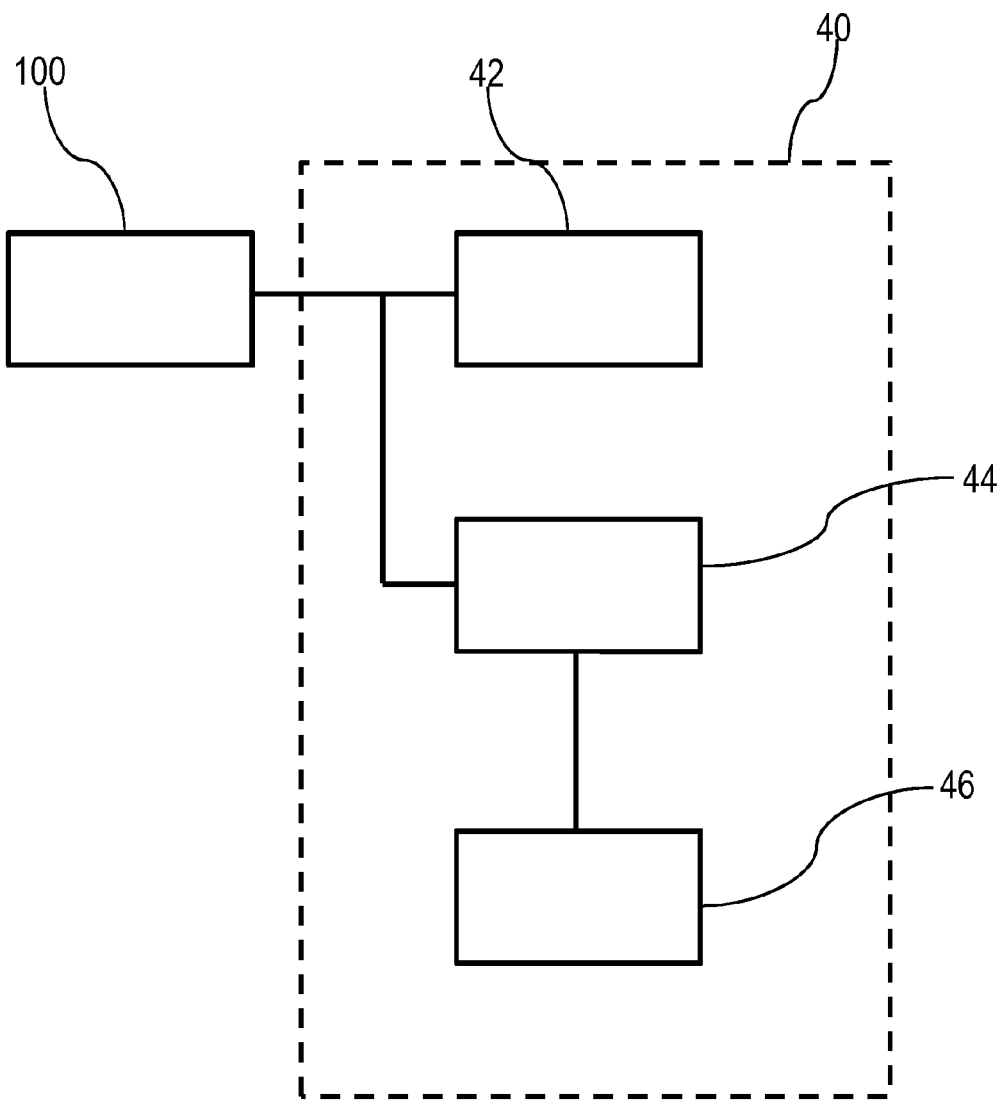
FIG. 4 shows a system diagram of a system for micro-scale spectroscopy using a AFM/NMR probe according to the present disclosure.

In at least one embodiment according to the present disclosure, the AFM subsystem 100 embodies a high-resolution, contact-mode scanning probe microscopy where tip 12 may be brought into proximity with a sample surface 60, such as a cell. As shown in FIG. 3, forces between the tip 12 and sample surface 60 cause deflection D of the cantilever beam 10, which responses according to Hooke's Law. Depending on the environment and sample being probed, the forces acting on the tip 12 and beam 10 may be mechanical contact forces, van der Waals forces, capillary forces, chemical bonding forces, Casimir forces, or electrostatic forces, among others. The deflection D of the beam 10 may be measured by the piezo-elements 16 attached to the top surface 17 of the beam 10. The piezo-elements 16 are known in the art and produce an electric charge when subject to a mechanical stress, such as a strain due to the deflection D of the beam 10. Based on the piezoelectric effect, a change of strain in the beam 10 on the horizontal axis leads to an open-circuit voltage on the axis normal to the top surface 17. The piezo-elements 16 may be electrically connected to contacts 14 mounted on the anchor 30, which enable electrical connection between the piezo-elements 16 and a deflection detection circuit 42 as shown in FIG. 4 to quantify the deflection D. The deflection detection circuit 42 may embody a conventional Wheatstone bridge or other suitable comparative resistance circuit.

Figure 5:
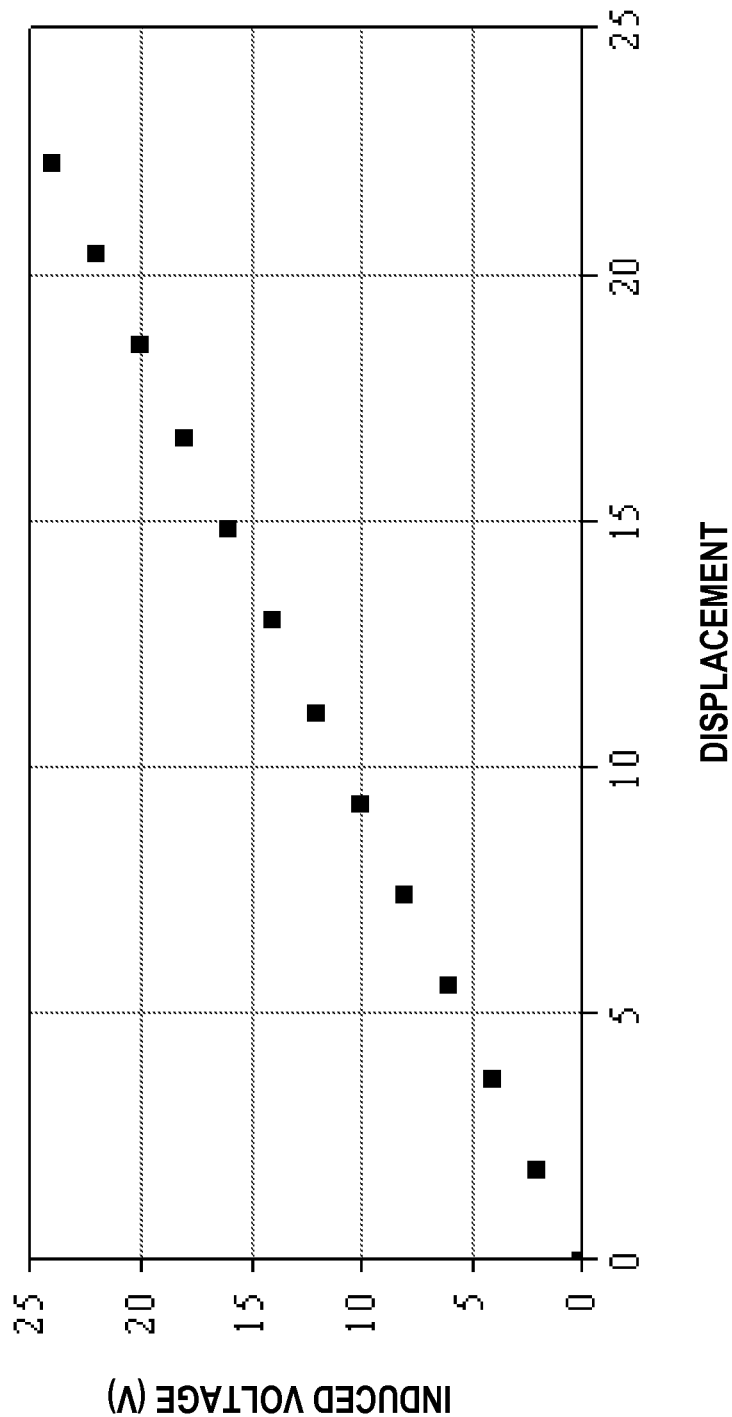
FIG. 5 shows a graph of induced voltage (measured in V) vs. displacement (measured in μm) a piezoelectric element of a AFM/NMR probe according to the present disclosure.

FIG. 5 shows the induced voltage in Volts (V) for a given deflection in microns (μm) for an embodiment of the present disclosure for the piezo-element 16 made of aluminum nitride, indicating that a deflection of 22.3 μm results in to stimulated voltage of 24 V. Area and thickness of piezo-elements 16 may vary the sensitivity and resolution of measured deflections. The piezo-elements 16 may be formed of any suitable piezoelectric material, including without limitation zinc oxide and aluminum nitride. In at least one embodiment of the present disclosure, the piezo-elements 16 may have dimensions 395 μm×50 μm×0.1 μm each.

Alternatively, deflection D in the beam 10 may be measured by means other than the piezo-elements 16, including without limitation laser deflection, optical interferometry, capacitive sensing, or other suitable method. The laser deflection method may include using a laser spot reflected from the distal end 11 of the top surface 17 of the beam 10 onto an array of photodiodes.

In at least one embodiment, the piezoelectric elements 16 may be capable of the small, highly-controlled movements and directional control of the tip 12 using the reverse piezoelectric effect. Accordingly, the tip 12 may be brought into contact with the sample cell 60 by appropriate excitation of the piezoelectric elements 16 integrated with the cantilever bean 10 for real-time feedback. Thus, the size of the sample cell 60 may be estimated, and the close proximity of the NMR subsystem 120 is thereby ensured as shown in FIG. 3. The use of piezoelectric-directed deflection of the probe can also facilitate three-dimensional surface imaging of the sample cell 60, since the distance between the NMR subsystem 120 and the sample 60 may be changed on demand, thereby tracking subtle, small-scale geometry in real time.

Figure 6B:
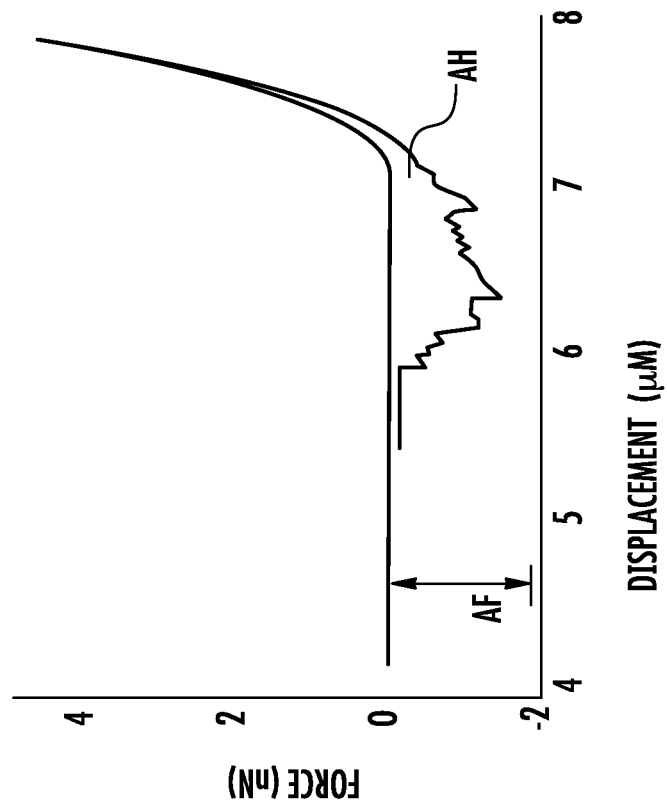
FIGS. 6A and 6B show schematic diagrams for determining stiffness and contact using a AFM/NMR probe according to the present disclosure.
Figure 6A:
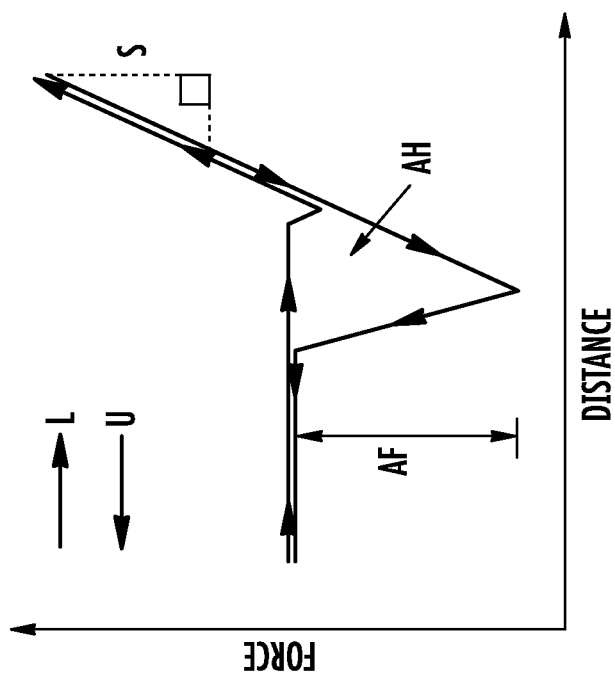

Consequently, the AFM subsystem 100 enables biophysical study of small structures, including the stiffness and adhesion of cells and substrates. As shown in FIGS. 6a and 6b, force-displacement curves may be obtained from each sample surface 60 using force calibration and tip displacement D, calculated as the difference between the z-position of the at least one piezoelectric element 16 and the deflection determined by the piezo-elements 16 after loading (represented by the direction arrow L). Stiffness may be determined from the slope of the curve S at the onset of unloading (represented by direction arrow U) from the maximum tip displacement D. Adhesion force AF may be measured as the pull-off force when the tip 12 separates from the surface 60 during unloading U. The area of the curve defining the difference in the loading (L) versus unloading (U) response of the AFM subsystem 110 represents an adhesion hysteresis AH. Importantly, diseased (e.g., arthritic) and aged cells exhibit increased stiffness, which can be detected by the AFM subsystem 110. Likewise, adhesion hysteresis AH may be correlated cell characteristics.

Due to the broad employment of AFM technology, there is a large variety of commercially available pre-manufactured AFM subsystems 110 with dimensions and stiffness suitable for biophysical studies, for example, from Bruker AFM Probes, Camarillo, Calif., and Applied NanoStructures Inc., Santa Clara, Calif. Such pre-manufactured AFM subsystems 110 may be modified by the fabrication of the NMR subsystem 120 thereon to form the integrated AFM/NMR probe 100 as described herein.

The hybrid AFM/NMR probe 100 further includes the NMR subsystem 120 integrated with the AFM subsystem 110 to form the AFM/NMR probe 100. The NMR subsystem 120 operates by the principles of nuclear magnetic resonance, by which the absorption and re-emission of electromagnetic radiation at the resonant frequencies of specific nuclei within a sample is detected by the radiofrequency coil 20 when the sample is placed in a magnetic field. For example, the resonant frequency of a particular substance is directly proportional to the strength of the magnetic field applied to the substance. In conventional NMR spectroscopy, the magnetic nuclear moments or spins of target nuclei within a sample to be analyzed are aligned by the application of a magnetic field. Once so aligned, a short pulse of radiofrequency electromagnetic radiation may be applied to the sample, which results in a titling and precession of the magnetization vectors away from their equilibrium positions transverse to the direction of the applied external magnetic field. As the out-of-equilibrium magnetization vector precesses about the external magnetic field vector at the magnetic resonant frequency of the nuclei spins, the oscillating magnetization vector may induce a current in a nearby pickup coil, creating an electrical signal oscillating at the NMR frequency. The resulting signal may be Fourier transformed using a spectrometer to obtain frequency-domain data that can be used in the analysis of sample. Importantly, diseased (e.g., osteoarthritic) and aged cells exhibit altered amplitudes in particular spectra, which can be detected by the NMR subsystem 120 to identify such cells.

Figure 7:
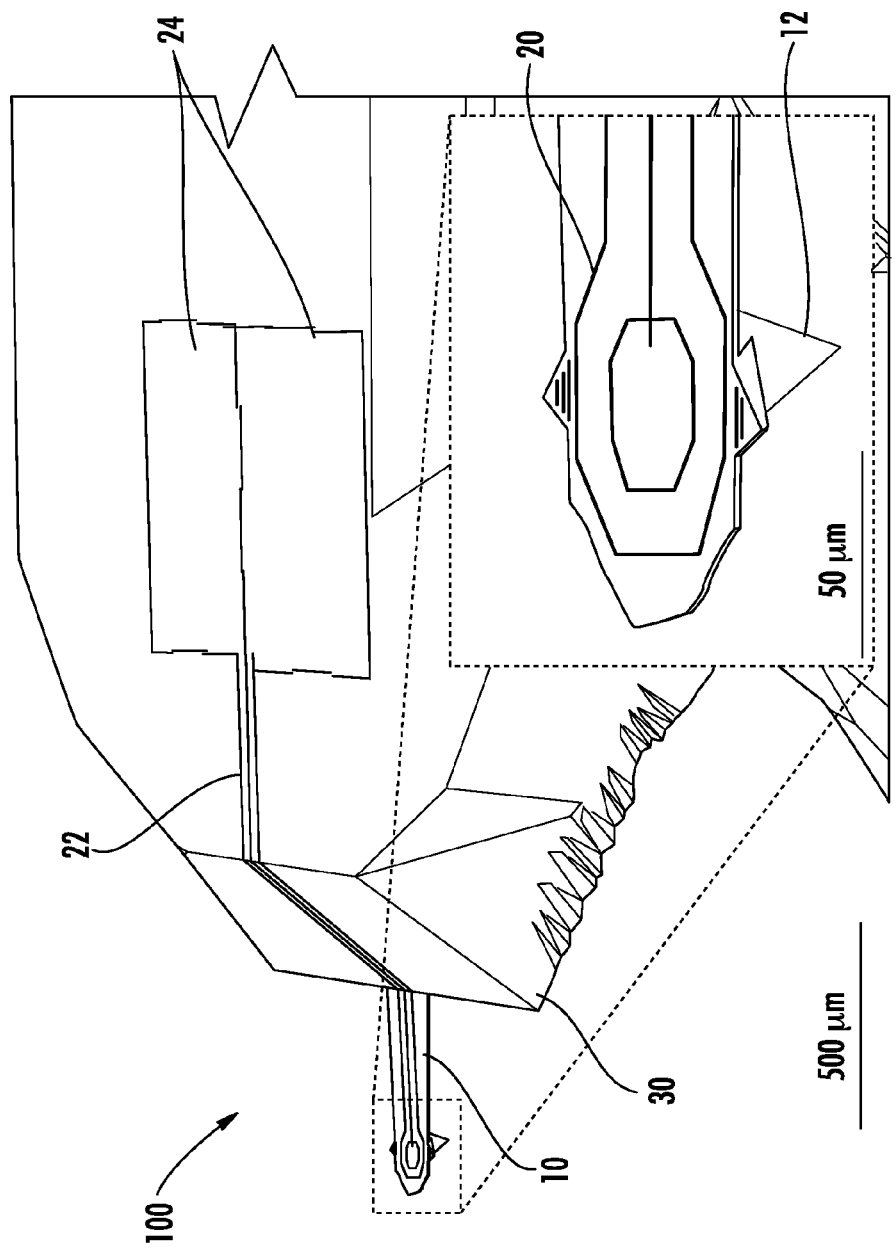
FIG. 7 shows perspective and detailed views of a AFM/NMR probe according to the present disclosure.

The NMR subsystem 120 includes a micro radiofrequency coil 20 mounted at the distal end 11 of the cantilever beam 10 opposite the tip 12. The coil 20 may be electrically connected by a pair of leads 22 extending axially along the beam 10 to a set of contacts 24 positioned adjacent the anchor 30. As shown in FIG. 4, the coil 20 may be electrically connected via the contacts 24 to a tuning circuit 44 and further to a spectrometer 46. The deflection detection circuit 42, tuning circuit 44, and spectrometer 46 may define a data acquisition system 40 electrically connected to the AFM/NMR probe 100. Further, the coil 20 may have a radius between 50 µM and 500 µm. The coil 20 may be substantially circular in shape or may be any suitable shape that allows for turns in the coil 20, for example octagonal as shown in FIG. 7.

Figure 8:
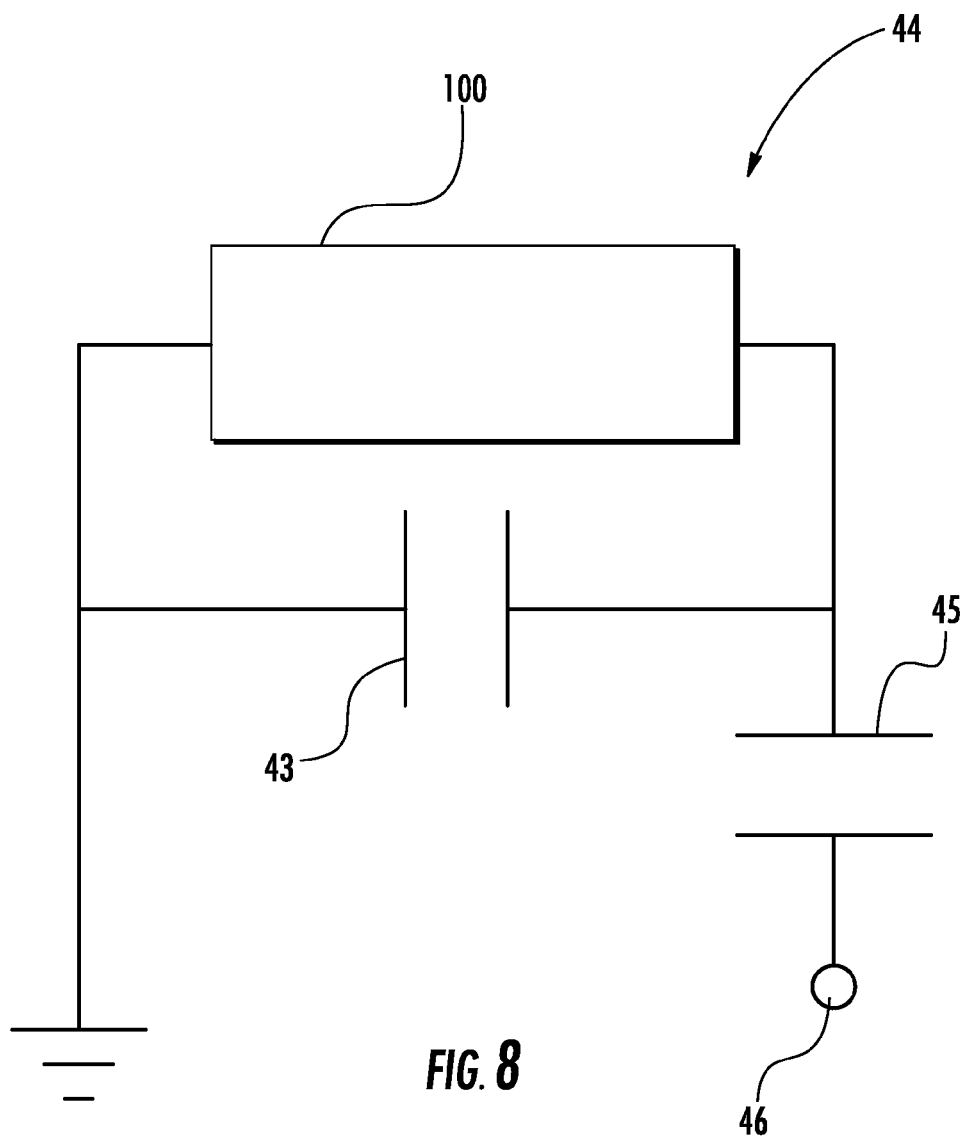
FIG. 8 shows a circuit diagram for a tuning circuit according to the present disclosure.

As shown in FIG. 8, the tuning circuit 44 may include a series capacitive matching circuit with tunable capacitors, 43 and 45, in which the AFM/NMR probe 100 is placed in parallel with a tuning capacitor 43 before running through a matching capacitor 45. The outputs of the tuning circuit 44 may be electrically connected to the spectrometer 46 and to ground. In at least one embodiment, the capacitance value of the tuning capacitor 43 may be 53 picofarads (pF) and of the matching capacitor 45 is 4 pF.

Figure 9:
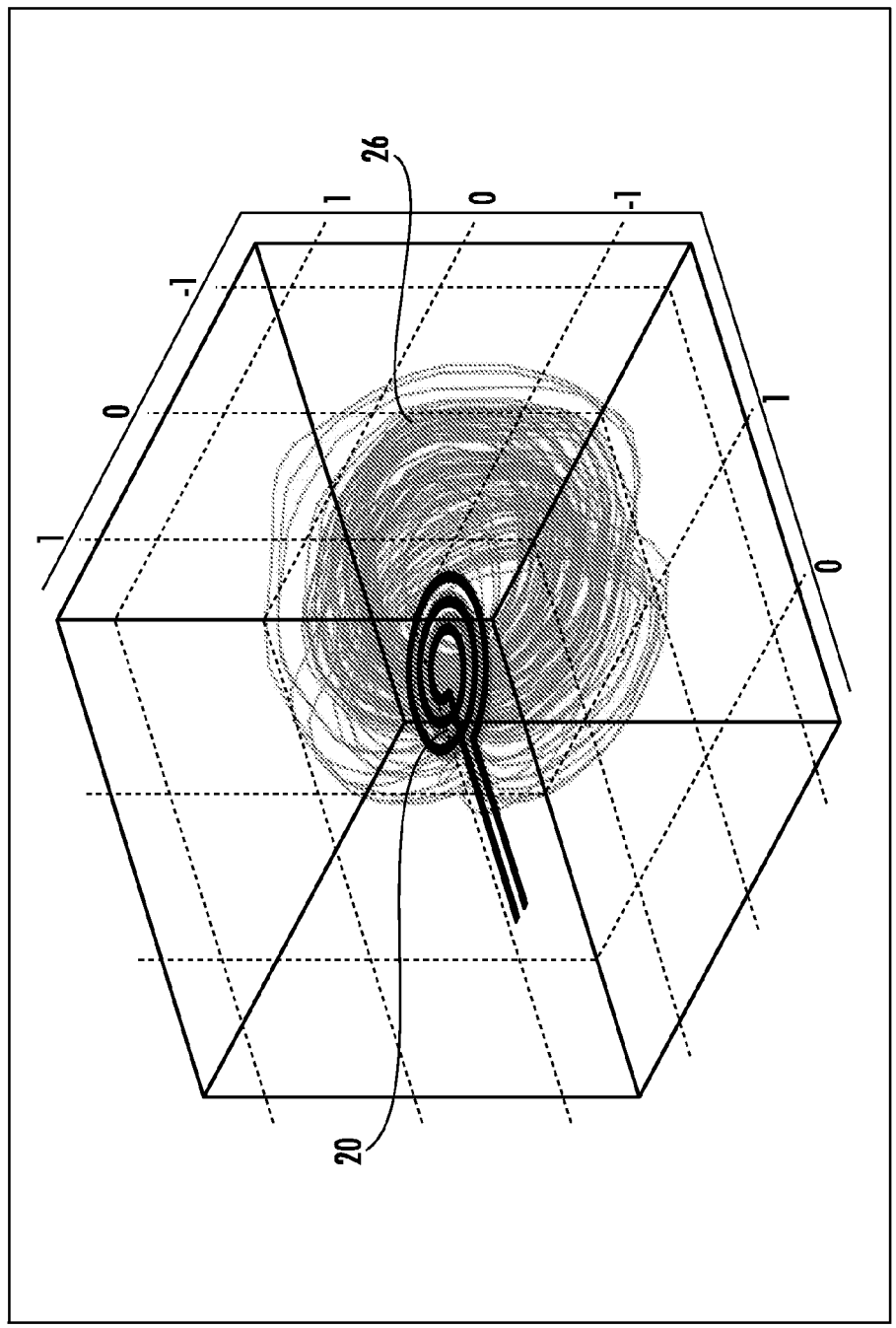
FIG. 9 shows a simulation of an electromagnetic field generated by a AFM/NMR probe according to the present disclosure.

The coil 20 may serve both as a transmitter and a receiver of radiofrequency radiation. As shown in FIG. 2, electric current may be applied the coil 20 to generate a near-field electromagnetic field 26 at or near the distal end 11 of the beam 10. FIG. 9 depicts magnetic flux lines of the electromagnetic field 26 generated by the coil 20 when energized in a transmitting mode. The distribution of magnetic flux lines for the planar coil 20 depends on the geometric parameters of the coil 20, such as number of turns, pitch distance between each turn, and the inner radius of the first turn, as well as the induced current in the coil 20. In receiving mode, the coil 20 conducts the current induced therein by the oscillating magnetization vectors of the nuclides within the sample 60 to the data acquisition system 40, where the signal is conditioned and analyzed.

Finite element analysis (FEA) may be used to estimate performance and optimize the design of the coil 20. The magnitude of the magnetic flux density (B) on a plane xz perpendicular to a direction y of the magnetic field may be calculated as:

$$B_{1,xz}(\vec{\tau}) = \sqrt{B_{1,x}^2(\vec{\tau}) + B_{1,z}^2(\vec{\tau})}$$

Figure 10A:
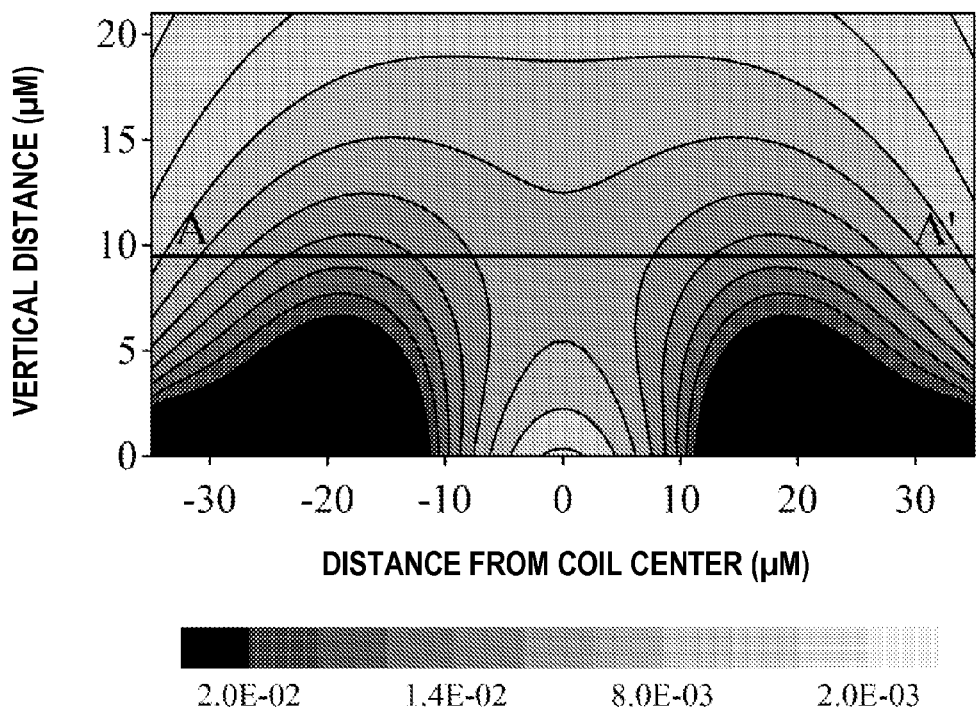
FIG. 10A shows a two-dimensional simulation of the variation in an electromagnetic filed generated by a AFM/NMR probe according to the present disclosure across a coil (as measured in μm) and at a distance from the coil (as measured in μm), where field strength is measured in Tesla.
Figure 10B:
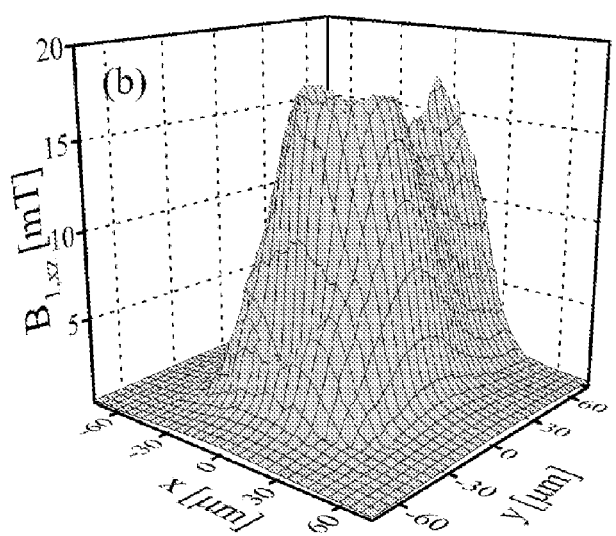
FIG. 10B shows a three-dimensional simulation of the variation in an electromagnetic filed generated by a AFM/NMR probe according to the present disclosure across a coil (as measured in μm) and at a distance from the coil (as measured in μm), where field strength is measured in milli-Tesla.

In at least one embodiment, the inductance and resistance of the coil 20 may be 0.86 nanohenry (nH) and 3.27 Ohms (Ω), respectively, given an input power to the 6.29 Watts (W). In at least one embodiment of the present disclosure, the impedance of the coil 20 may range from 100 pH to 25 nH with the input power ranging up to approximately 50 W. As shown in FIGS. 10a and 10b, the magnetic flux density of the field 26 may vary spatially on the plane of the coil 20 and perpendicular to the static, applied magnetic field. FIG. 10a depicts the vertical limit of the sensing volume 28 as a line A-A'. FIG. 10b shows the magnitude of the field 26 at a plane parallel to the coil 20 at the line A-A', with the axis of the applied magnetic field being along the y-axis. The applied magnetic field may be varied. Exemplary magnetic field strengths may be 1.5, 3.0, 4.7, 7.0, 9.4, 11.7, 14.1, and 18.8 Tesla (T), which correspond to the following resonant frequencies for hydrogen protons (1H): 64, 128, 200, 300, 400, 500, 600, 800 MHz, respectively.

The field 26 defines a sensing volume 28, which represents the range limit of the NMR subsystem 120. Where the coil 20 is a circular coil of radius α, the sensing volume 28 is defined as:

$$Z \leq \frac{a}{2} \text{ and } x \leq a$$

where z is the axis normal to the coil plane and x is the axis on the coil plane vertical to the static magnetic field. Where the inner area of the coil 20 may be assumed to be an ellipse, the sensing volume 28 can be approximated by the volume given by the ellipse area times half the radius of the minor axis. Therefore, in at least one embodiment of the present disclosure, the threshold sensing distance may be 8 µm, which is adequate for in-cell NMR measurements, and the overall sensing volume 28 on each side of the coil 20 may be 9,700 µm³ (or 9.7 picoliters (pL)). Assuming an average diameter of 20 µm for mammalian cells and a cell volume of 33,500 µm³ (33.5 pL), the AFM/NMR probe 100 is capable of in-cell NMR signal detection. Because the inner diameter of the coil is less than 100 µm, the attained resolution is in the range of micrometers.

Figure 11:
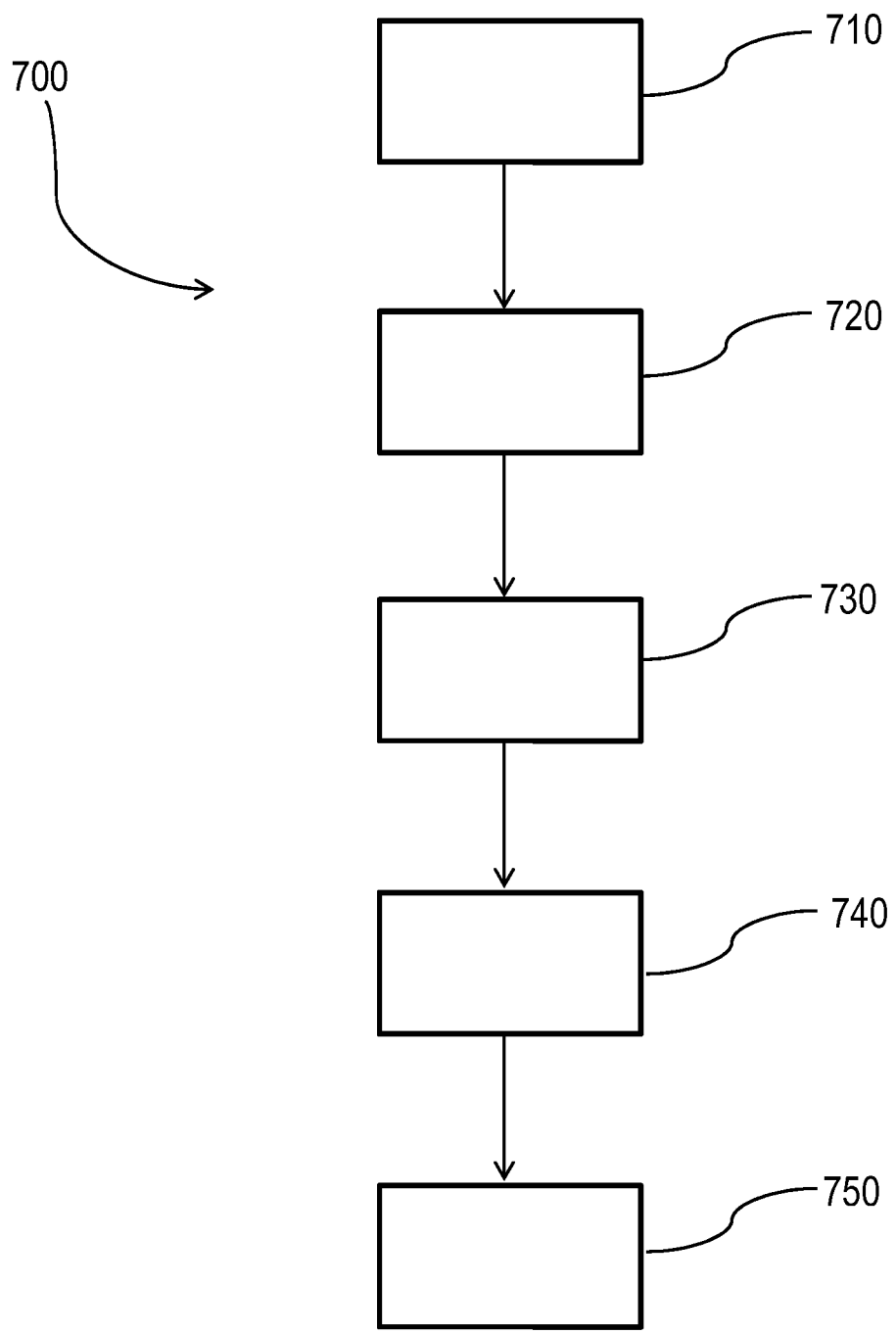
FIG. 11 shows a method for fabricating a AFM/NMR probe according to the present disclosure.

The design and fabrication of the planar coil 20 and associated components of the NMR subsystem 200 may be formed by nanofabrication techniques to achieve the necessary signal to noise ratio (SNR) for the resulting NMR signal, as described herein. One such technique employs focused ion beam (FIB) milling. FIG. 7 shows an embodiment of a AFM/NMR probe 100 formed by a FIB method 700. Referring to FIG. 11, the FIB method 700 may include a step 710 of applying a thin, uniform insulation layer of Parylene-C to a pre-manufactured silicon AFM subsystem 110 to provide electrical insulation between the silicon and the later-formed coil 20, leads 22, and contacts 24, thereby eliminating parasitic effects and current leakage. In at least one embodiment, the insulation layer may be formed of polyimide, silicon nitride, or most parylenes, for example, Parylene-N, -D, or -HT. The insulation layer may range in thickness between 10 nm and 100 nm. The FIB method 700 may include a step 720 of applying a thin layer of conductive material to the entire top surface 17 of the beam 10 via radiofrequency plasma sputtering or other suitable deposition process known in the art. In a least one embodiment, the conductive layer may include a 5 nm-thick base layer of titanium under a 100 nm-thick layer of gold. In at least one alternative embodiment, the conductive layer may be formed with a combination of chrome or titanium as a base layer and platinum or gold as the top layer, where the base layer may range from 5 nm to 10 nm and the top layer may range between 100 nm and 1.5 µm. The FIB method 700 may further include a step 730 of FIB milling to etch and define the turns of coil 20, leads 22, and contacts 24. The FIB milling process enables definition of the coil 20 and other features without inducing stress in the cantilever beam 10 that could lead to undesired bending of the beam 10. The FIB method 700 may further include a step 740 electrically connecting the PCB 32 to the contacts 24 and the contacts 14 of the AFM subsystem 110. However, FIB milling may not be the most cost-effective method of forming the NMR subsystem 200 on the AFM subsystem 110 due to the serial nature of the process, poor adhesion of the conductive material layer in some cases, and the potential for parasitic effects, such as eddy currents, because of the presence of unused conductive regions isolated but not removed by the FIB process.

The FIB method 700 shown in FIG. 11 may produce a coil 20 with only one turn, which is adequate for basic functionality. To achieve a coil 20 with multiple turns, the FIB method 700 may include a step 750 including deposition of successive layers of insulation material, such as Parylene-C, with FIB-etching of connection sites to bridge from coil turn to turn and intervening layers of conductive material to form each coil turn and the connection to the lead 22. In at least one embodiment of the present disclosure, the tip 12 may be attached beneath or on top of the coil 20.

Figure 12:
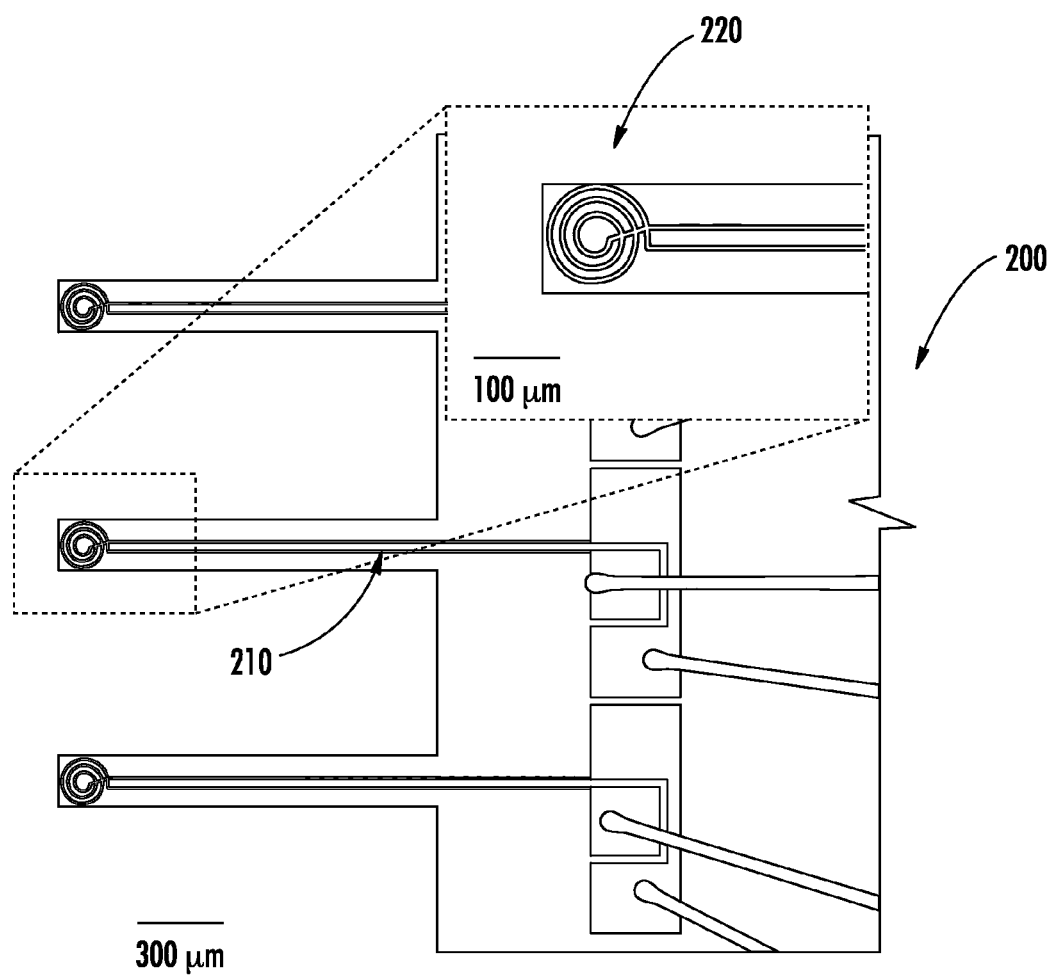
FIG. 12 shows perspective and detailed views of several AFM/NMR probes according to the present disclosure fabricated by a batch method.
Figure 13:
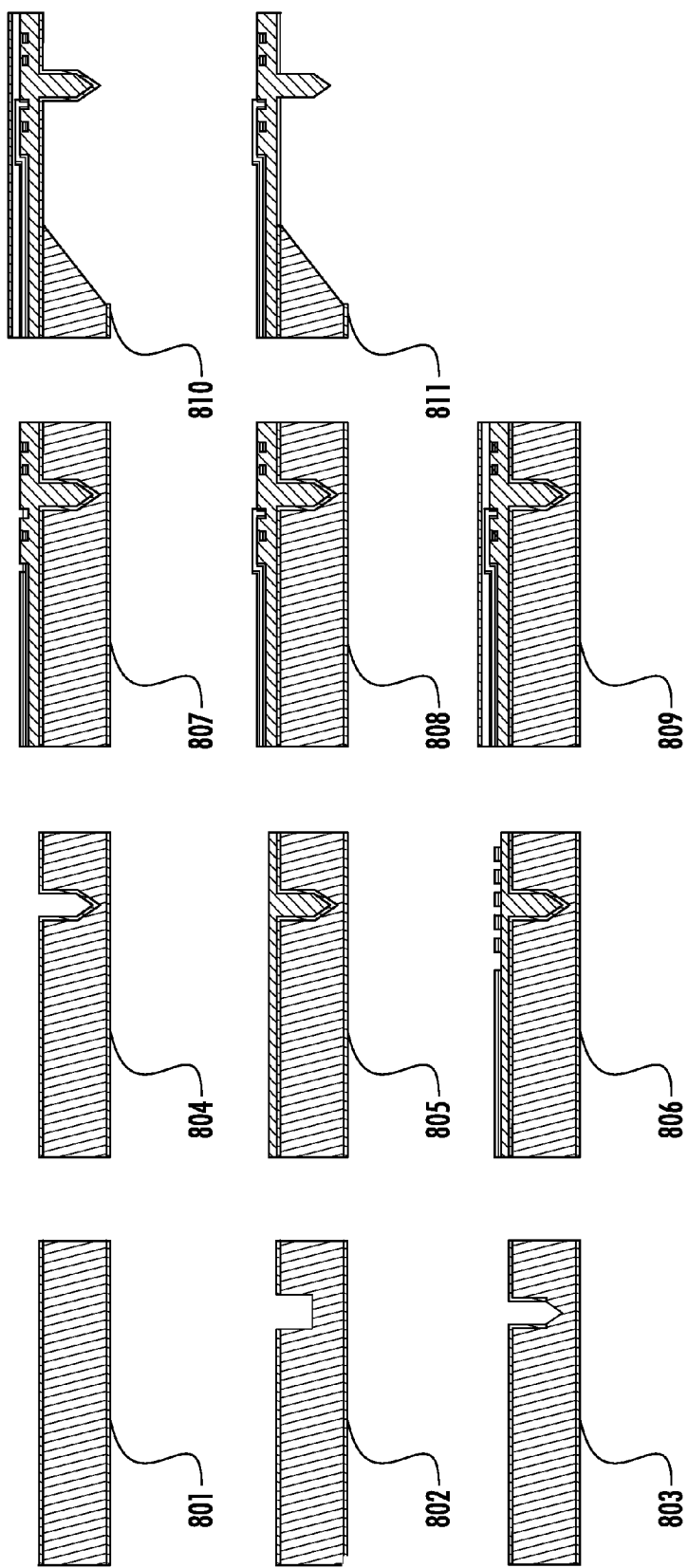
FIG. 13 shows a method for fabricating a AFM/NMR probe according to the present disclosure.

Alternatively, as shown in FIG. 12, multiple AFM/NMR probes 200 may be formed by a batch method 800, in which a plurality of AFM subsystems 210 are first formed, then a NMR subsystem 220 is formed on each AFM subsystem 210 by a conventional lift-off process to define the coil, leads, and contacts of each NMR subsystem 220. Referring to FIG. 13, the batch method 800 may include a step 801 providing a silicon wafer with an oxide layer, such as silicon oxide. In at least one embodiment, the oxide layer maybe 0.7 µm thick. In a step 802, the oxide-coated silicon wafer may then be micromachined using a deep reactive-ion etching (DRIE) process, or other suitable process, to form the opening for tip 12. The batch method 800 may include a step 803 of coating the side walls of the opening with a layer of thermal oxidation of silicon, reactive-ion etching of the bottom of the opening to enable tip formation, and then forming the tip 12 by a wet etching process using tetramethylammonium hydroxide (TMAH) or other suitable solvent.

The batch method 800 may further include an additional silicon oxide deposition in a step 804 to protect the newly-formed tip opening. Subsequently, a 2 µm-thick layer of silicon nitride may be deposited in a step 805 along the top surface of the wafer using plasma-enhanced chemical vapor deposition (PECVD) or other suitable process, thereby filling the opening to form the tip 12 and forming the structural features of the cantilever beam 10. The batch method 800 may include an optional chemical-mechanical polishing step 805b to ensure the beam 10 is planar. The batch method 800 may further include a step 806 in which a layer of gold is deposited on the silicon nitride layer and wet etched to pattern the coil 20 and one lead 22. In at least one embodiment, the gold layers of the method 800 may be 0.1 µm thick. The batch method 800 may include a step 807 of sputtering the gold layer with silicon nitride and wet etching holes to enable electrical connection to the coil 20 to the other lead 22. A step 808 of the batch method 800 may include depositing an additional layer of gold to form the electrical connection between the coil 20 and the other lead 22. The batch method 800 may include a step 809 of using PECVD to form layers of silicon nitride and silicon oxide on the top surface 17 of the newly-formed beam 10. The batch method 800 may further include a step 810 of releasing the cantilever beam 10 by dissolving the silicon surrounding the tip 12 using potassium hydroxide or other suitable solvent. A step 811 may include removing the underlying silicon oxide layer using a hydrogen fluoride etch process to complete formation of the tip 12. The batch method 800 may further include a step 812 of applying a submicron passivation layer of Parylene-C in insulate the exposed surfaces of the coil 20, leads 22, and contacts 14, 24.

The advantages of the batch method 800 include the fact that the fabricated tip 12 does not protrude out of the top surface 17, thereby allowing for surface machining and eliminating the need for expensive silicon-over-insulator wafers. In addition, the batch method 800 enables for parallel processing and fabrication of multiple AFM subsystems 210 on a single silicon wafer, thereby improving fabrication efficiency and reducing overall fabrication costs. Further, AFM/NMR probes 100 fabricated by the batch method 800 may result in sensing volumes 28 ranging approximately between 49 pL and 49 mL for coils 20 ranging from 50 µm and 500 µm, as compared the FIB method 700, which results in sensing volumes 28 of approximately 19.4 pL.

In at least one embodiment of the present disclosure, the tip 12 may be a separate component that is bonded to the beam 10 with epoxy glue, thereby enabling the tip 12 to be spherically shaped, which aids in protecting the surface of the sample 60 from protrusion or damage. Attachment of separate tip 12 may be incorporated in the batch method 800 by skipping the steps of the silicon nitride tip formation (i.e., the masking, DRIE, and filling of the opening for the tip 12 in steps 802-805) and attaching the tip 12 in the steps 809 or 811.

Figure 14:
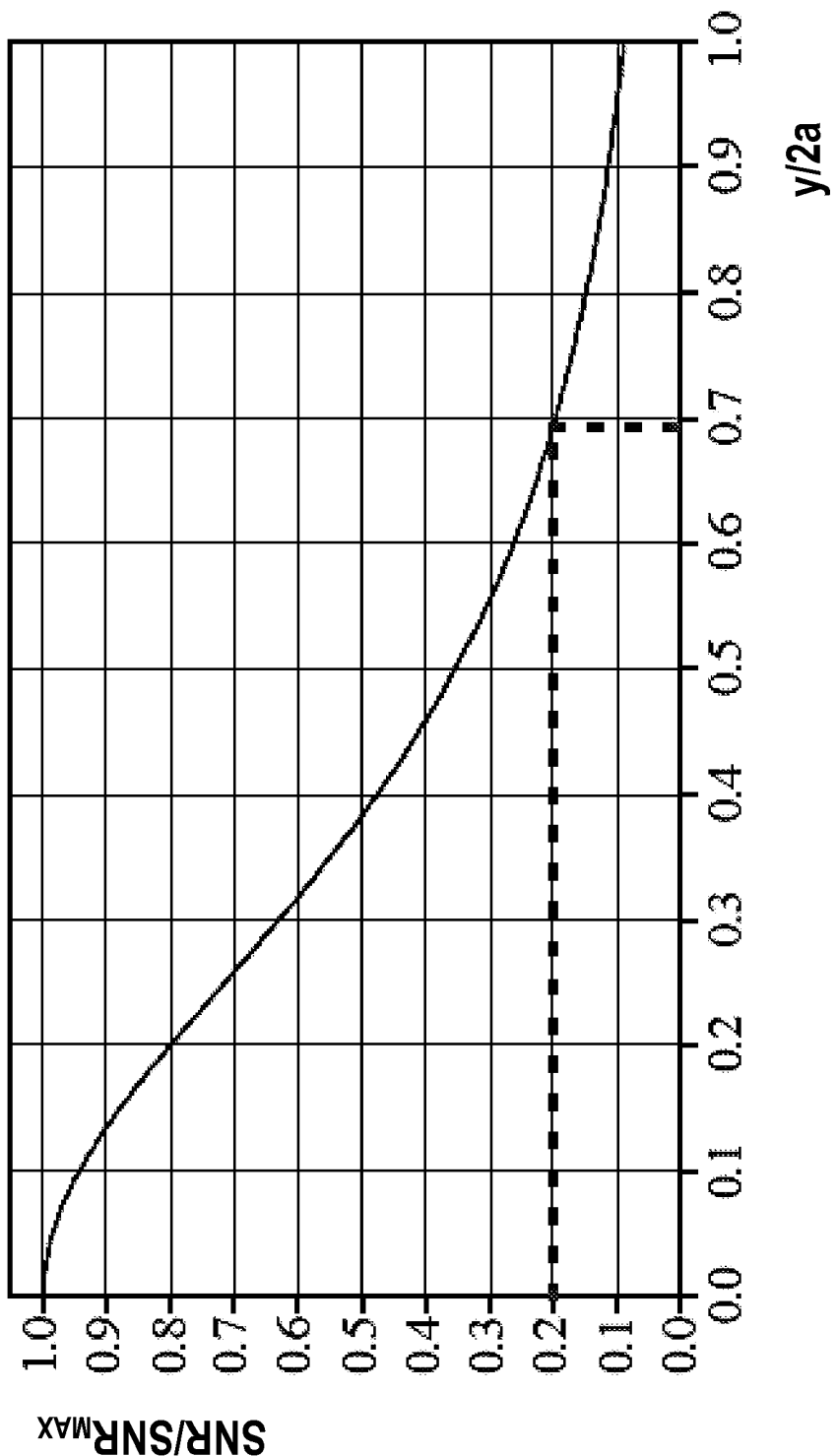
FIG. 14 shows a graph of signal-to-noise ratio versus non-dimensional distance from a AFM/NMR probe according to the present disclosure.

Because the strength of the magnetic field 26 diminishes quickly as the distance from the center of the coil 20 increases, the length of the tip 12 may be limited to not significantly hamper attaining an adequate signal-to-noise ratio (SNR). For planar coils, the transverse magnetic field $B_T$ is given by:

$$B_T = (\mu_0 I/4) a^2 / (a^2 + y^2)^{3/2}$$

where, I is current provided to the coil, a its radius, and y the vertical distance from the coil's plane. The targeted maximum length of the tip may be equal to the distance y where the magnetic field strength $B_T$ is 20% of its maximum value (i.e., the value for y=0). By normalizing the field strength, this value is approximately equal to 1.4 a. Because the attained SNR is directly proportional to the strength of the transverse magnetic field, the corresponding value of the SNR at that point, may be equal to 0.2 times SNR. The change of SNR versus distance from the center of the coil is plotted in FIG. 14. For example, for a coil 20 with internal radius of 100 µm, the maximum allowed length of the tip would be 80 µm. In order to be able to acquire a full spectrum of the sample 60 assuming a sample diameter of 25 µm, the height of the tip may be 55 µm minus the thickness of the cantilever beam 10. As shown from these calculations, the presence of the AFM tip 12 may not negatively impact the acquisition of localized spectroscopy in single cell samples 60 as long as the coil size is selected appropriately. Furthermore, the data presented illustrate the capability of microfabricated coils 20 on an AFM cantilever beam 10 to ensure adequate resolution for the biochemical studies of cells through NMR, while the biophysical parameters are acquired through the AFM response with the contact of the tip 12 to the sample cell 60.

Figure 15:
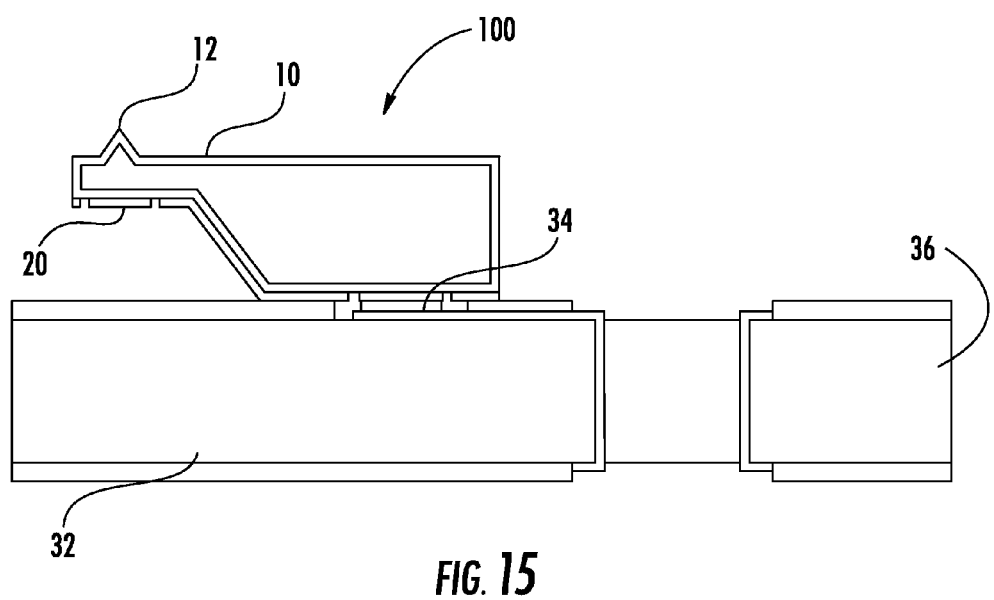
FIG. 15 shows a side view of a AFM/NMR probe according to the present disclosure.

Once fabricated, the finished AFM/NMR probe 100 may be mounted to a custom-designed printed circuit board (PCB) 32 with a conductive adhesive 34 (such as, without limitation, 118-09A/B-187, Creative Materials Inc., Tyngsboro, Mass.) using a conventional flip-chip bonding process. The flip-chip bond may be secured with epoxy, and a connector 36 may be soldered to the PCB 32 as shown in FIG. 15.

Figure 16:
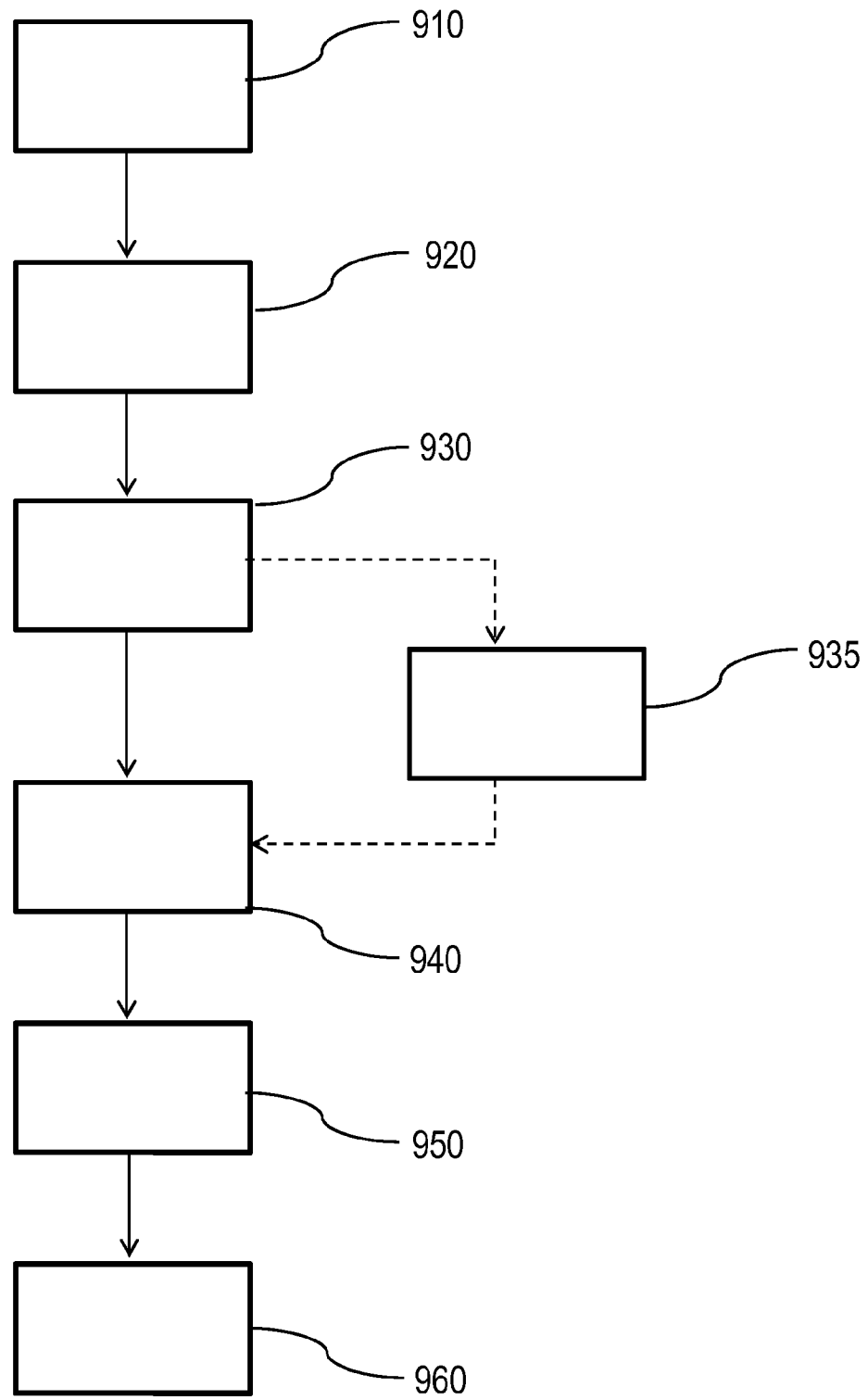
FIG. 16 shows a method for using a AFM/NMR probe according to the present disclosure.

The AFM/NMR probe 100 improves the biochemical profiling of topographical and biophysical information attained using AFM-based platforms, by incorporating a planar micro-coil 20 on top of AFM cantilever beam 10 to generate a NMR signal. The AFM/NMR probe 100 thereby enables nanoscale spatial localization, as well as the biophysical and physicochemical analysis features of AFM, combined with the noninvasive, localized spectroscopic and imaging capabilities of NMR for the real-time microscopy and structural analysis of single cells. As shown in FIGS. 3 and 16, an analysis method 900 using the AFM/NMR probe 100 may include a step 910 of introducing the AFM/NMR probe 100 into a volume to be analyzed (e.g., within a patient's body or within a volume containing a sample 60) and directing the AFM/NMR probe 100 to location to be analyzed. A step 920 of the analysis method 900 may include positioning the tip 12 of the AFM/NMR probe 100 in contact with a sample surface at the location to be analyzed and using deflection of the beam 10 as measured by piezo-elements 16 as feedback from the AFM subsystem 110 to confirm contact. The analysis method 900 may include a step 930 of lateral scanning the sample surface by translating the tip 12 across the surface, thereby ensuring the close proximity of the coil 12 to the sample cell 60 and, optionally, acquiring AFM/NMR data at multiple locations surface of the sample. Accordingly, the use of piezo-electric-based deflection of the AFM subsystem 110 may also enable three-dimensional surface imaging of biophysical surface characteristics, such as morphology and adhesion, because the tip 12 may be maneuvered to track subtle and small scale geometry in real time.

The analysis method 900 may further include a step 940 of applying an external high-frequency magnetic field to the location under analysis and emitting one or more electromagnetic pulses from the coil 20. The analysis method 900 may further include the step 950 of using the coil 20 to receive the NMR signal emitted by the sample nuclei, resulting from the applied electromagnetic pulse in the applied magnetic field. In at least one method according to the present disclosure, the high-frequency magnetic field may have a strength of 11.7 T, and the electromagnetic pulses may be 5 μs, 90° pulses with an acquisition time of 1.64 seconds (sec) and a delay of 1 sec. A step 960 of the analysis method 900 may include conducting Fourier transform spectroscopy on the NMR signal received by the coil 20 to determine the biochemical characteristics of the sample.

The analysis method 900 may include an optional step 935 of attaching the cell sample 60 with an applied surface chemistry, including without limitation fibronectin, poly-1-lysine, or collagen coating known within the art, which may promote cell adhesion and proliferation. The electromagnetic pulses of step 940 may include novel pulse sequences for rapid imaging to overcome potential confounding problems with local diffusion while allowing for maximum SNR in small sample volumes. Further, positioning of the AFM/NMR probe 100 during interleaved imaging may create an effected phase-arrayed coil design 20.

Example

One embodiment of the AFM/NMR probe 100 according to the present disclosure was used to perform trial analyses and demonstrate operation of the AFM/NMR probe 100 with particular focus on evaluating SNR and linewidth of the signal acquired by the coil 20 in the receiving mode. For the trial, a coil 20 having five turns with an inner radius of 46 μm and an impedance of 12.8 nH was tuned and matched using a frequency sweeper and the tuning circuit 44 at the frequency of the applied high field magnet of 500 MHz (Bruker 500 MHz, Oxford Instruments). The capacitance values of the tuning 43 and the matching 45 capacitors were 53 pF and 4 pF, respectively. After matching and tuning, the AFM/NMR probe 100 was electrically connected to a 500 MHz Bruker NMR spectrometer 46 (Bruker DRX500), which was set to the following parameters: frequency: 500.13 MHz; high power pulse time: 20 μs; acquisition time: 1.19 sec; relaxation delay: 0.69 sec; number of scans: 1; sweep width: 7507.51 Hz.

Figure 17:
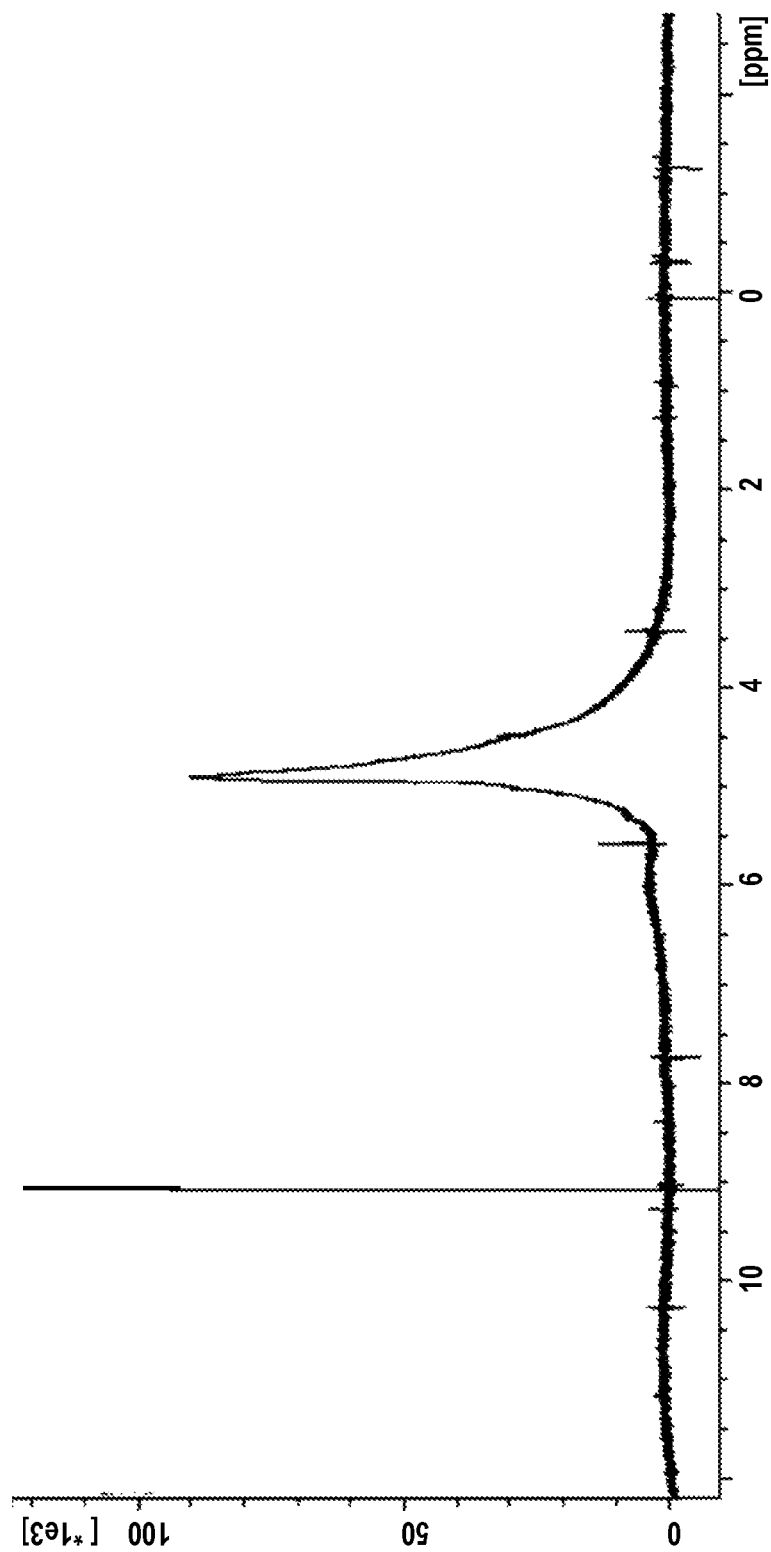
FIG. 17 shows a graph of signal-to-noise ratio for deionized water using a AFM/NMR probe according to the present disclosure.

The preceding set up of the AFM/NMR probe 100 and data acquisition system 40 was then exposed to a solution of deionized water. To generate the NMR signal, the coil 20 was energized with a single pulse for spin excitation and signal acquisition. During the relaxation delay, the coil 20 was switched to receiving mode, and the NMR signal was acquired via the coil 20 and data acquisition system 40. Subsequently, the SNR of the acquired NMR signal was determined. FIG. 17 shows the attained SNR of the acquired NMR signal after shimming and phase correction, which yielded a SNR of 66.7 with a linewidth of 125 Hz. These results demonstrate miniaturization of the sample volume 26 and cellular-scale localization of a NMR resonant signal.

Figure 18:
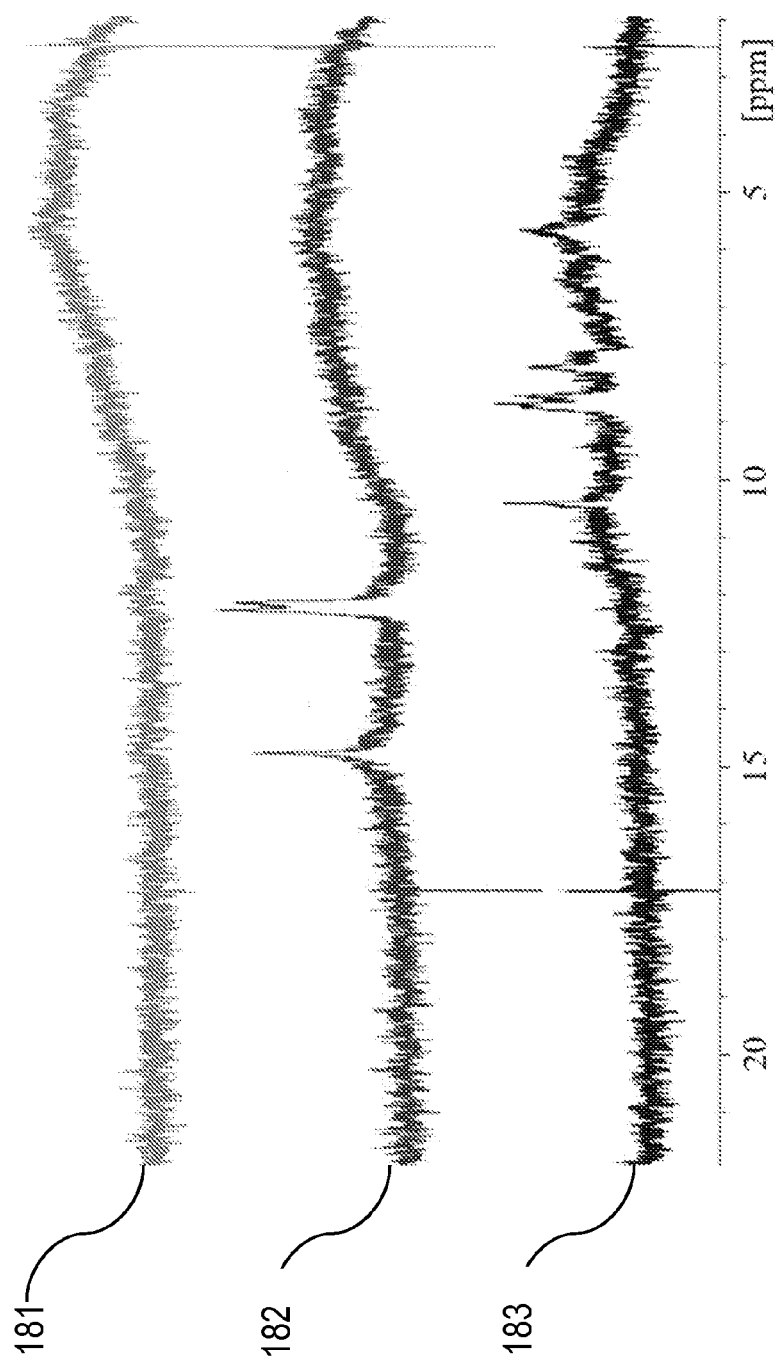
FIG. 18 shows a graph of signal-to-noise ratio for multiple type of samples water using a AFM/NMR probe according to the present disclosure.
Figure 19:
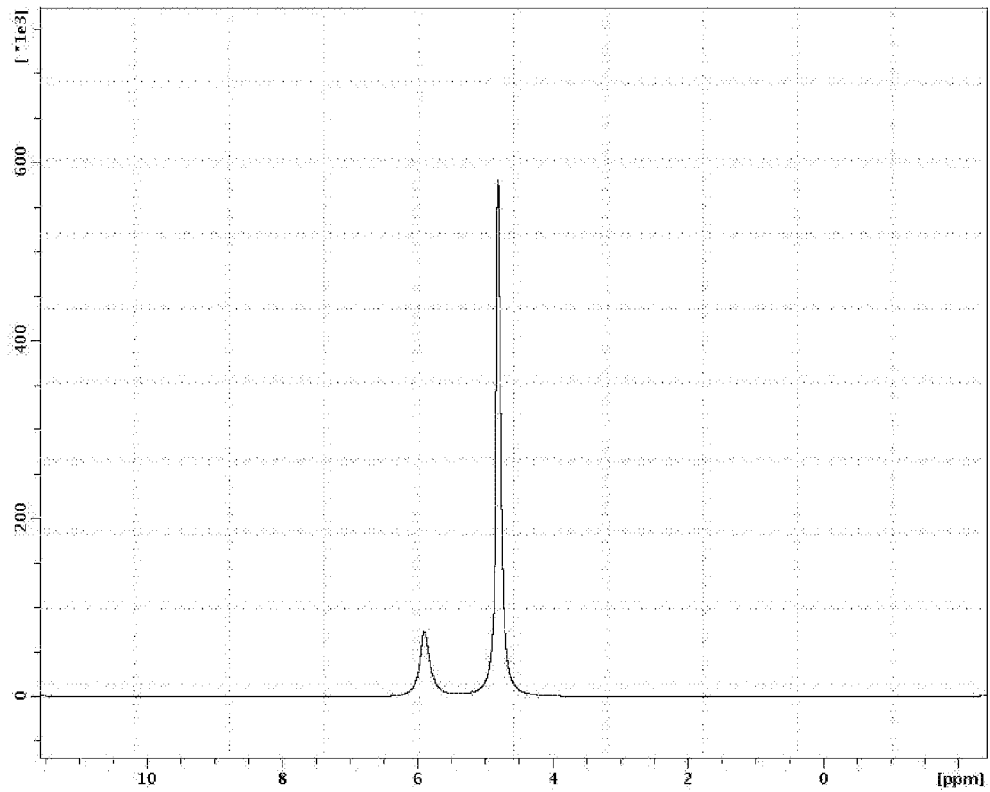
FIG. 19 shows a graph of signal-to-noise ratio for urea using a conventional NMR probe according to the present disclosure.

Subsequently, three additional liquids were analyzed evaluate an embodiment of the AFM/NMR probe 100: deuterium oxide, isopropanol alcohol, and urea. Multiple controls of deuterium oxide were used to confirm the performance of the AFM/NMR probe 100. In addition, any parasitic contribution of the interconnection wiring on signal detection was eliminated through acquisition experiments where the AFM/NMR probe 100 was bypassed but loaded with a sample 60. FIG. 18 shows the acquired signals for the control deuterium oxide 181, deionized water 182, and isopropanol alcohol 183. None of the acquired signals 181, 182, 183 has a flat baseline of the spectrum throughout the whole frequency range. Without being held to a specific theory, the broad feature in the spectrum shape may be attributed to the Parylene-C, which was used for electrical insulation in the FIB fabrication process 700. Consequently, AFM/NMR probes 100 fabricated using the batch method 800 are not anticipated to produce the broad feature. In addition, the acquired signals for deionized water 182 and isopropanol alcohol 183 show unexpected peaks for the deionized water and isopropanol alcohol samples. Without being held to a specific theory, the unexpected peaks may be attributed to a non-homogeneous field distribution. Such field inhomogeneity may be addressed and reduced by improved shimming, and therefore optimizing, of the acquisition signal, by adjusting the tuning circuit 44, and by employing a fluorinert liquid. FIG. 19 shows the frequency response of a conventional NMR probe in a solution of urea with expected results. Such a solution, i.e. with multiple distinct sources of 1H, in conjunction with an appropriate pulse sequence for the acquisition of multiple $T_2$s, e.g., the CPMG (Carr-Purcell-Meiboom-Gill) sequence known within the art, can be used with the AFM/NMR probe 100 in illustrate to study the cell composition and therefore provide information about its biochemical profile.

Figure 20:
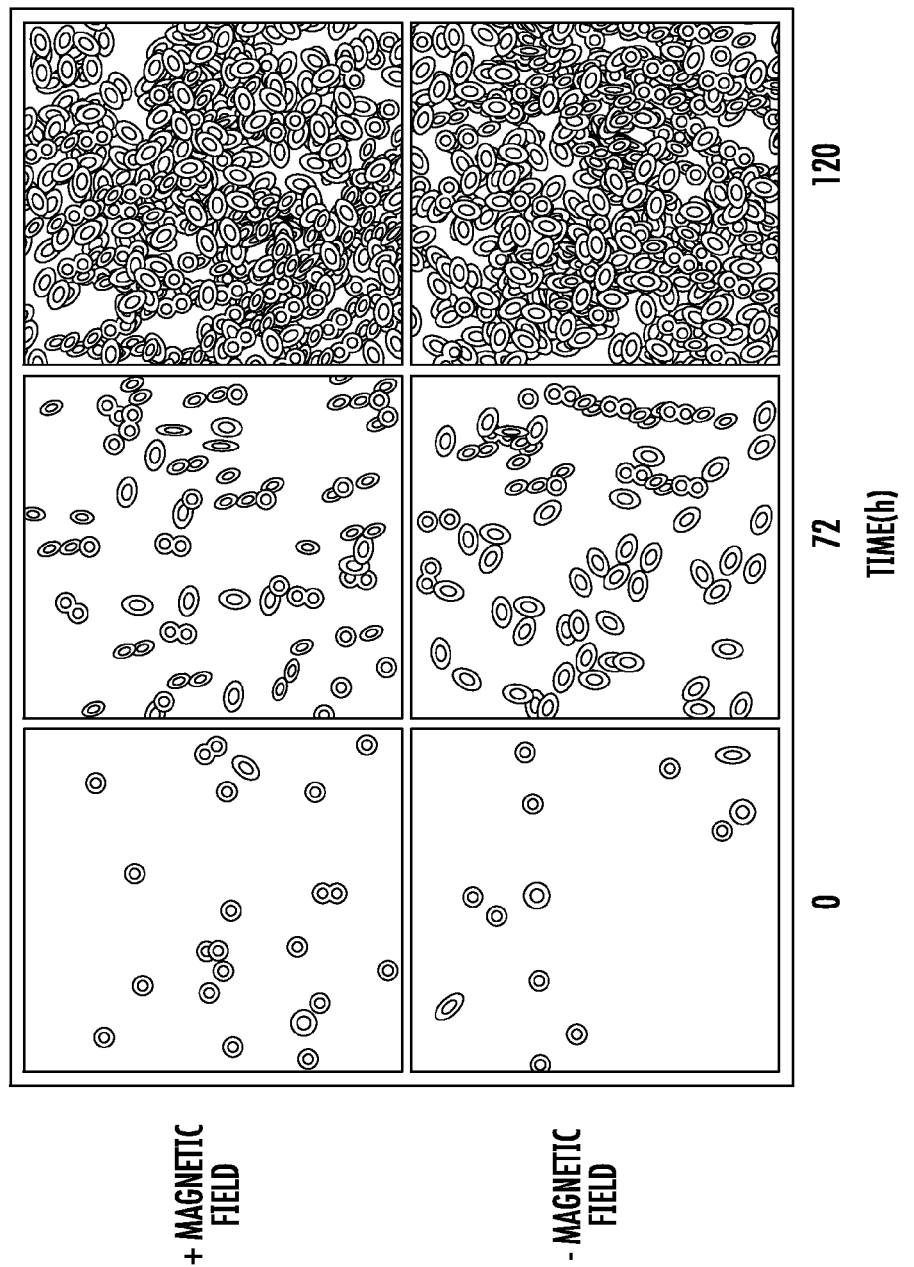
FIG. 20 is a schematic diagram depicting primary cells which may be grown to confluency for AFM/MRM studies.

Importantly, magnetic field exposure does not influence cell viability, as assayed by cell proliferation. To demonstrate the lack of effect on cell cultures, healthy bovine chondrocytes were harvested, cultured, and plated at $10^6$ cells/mL on polystyrene dishes. Cell viability was confirmed following one hour of 9.4 T exposure to a magnetic field using a cell count assay as shown in FIG. 20. Proliferation was unchanged by the magnetic field until confluency. Bovine primary chondrocytes were cultured in defined medium over 120 hours following 9.4 T exposure.

The potential applications of the AFM/NMR probe 100 technology are broad, including improved characterization of diseased or regenerative single cells and the study of complex cell and tissue system sensing, communication, growth, morphogenesis, remodeling, and apoptosis.

Those skilled in the art will recognize that numerous modifications can be made to the specific implementations described above. Therefore, the present disclosure is not to be limited to the specific embodiments illustrated and described above.

We claim:

1. A device for micro-scale spectroscopy, the device comprising:
   a beam having a distal end, a proximal end, a top surface and a bottom surface, the beam being attached to an anchor at the proximal end and further comprising a tip extending substantially perpendicular from the bottom surface at or near the distal end; and
   a coil having at least one turn mounted to the top surface of the beam at or near the distal end opposite the tip, wherein the coil is capable of both transmitting and sensing electromagnetic radiation.

2. The device of claim 1, wherein the beam further comprises:
   at least one piezoelectric element mounted to the top surface of the beam at or near the proximal end, wherein the at least one piezoelectric element is capable of generating a deflection signal due to strain in the beam due to a deflection of the distal end and of moving the distal end; and
   at least two piezo contacts electrically connected to the at least one piezoelectric element and disposed adjacent to the anchor.

3. The device of claim 1, wherein the tip is formed integral to the beam.

4. The device of claim 1, wherein the coil further comprises:
   two ends;
   at least two leads electrically connected to the coil, wherein at least one lead is connected to each of the two ends; and
   at least two coil contacts electrically connected to the at least two leads and disposed adjacent the anchor.

5. The device of claim 1, wherein the beam is formed of a silicon material.

6. The device of claim 1, wherein the beam is no more than approximately 2 microns thick.

7. The device of claim 1, wherein the beam has a spring constant between approximately 0.01 and 1.0 newtons per meter.

8. The device of claim 1, wherein the tip is spherically shaped.

9. The device of claim 1, wherein the beam and coil comprise a probe, the probe being capable of identifying biophysical and biochemical characteristics of a sample contacted by the tip of the probe.

10. The device of claim 9, wherein the probe is capable of determining a morphology of the sample.

11. The device of claim 9, wherein the probe is capable of isolating intercellular structures within a cell contacted by the tip of the probe.

12. A system for micro-scale spectroscopy, the system comprising:
   a probe, the probe comprising:
      a beam having a distal end, a proximal end, a top surface and a bottom surface, the beam being attached to an anchor at the proximal end and further comprising a tip extending substantially perpendicular from the bottom surface at or near the distal end,
      a coil having at least one turn mounted to the top surface of the beam at or near the distal end opposite the tip, wherein the coil is capable of both transmitting and sensing electromagnetic radiation,
      at least two leads electrically connected to the coil,
      at least two coil contacts electrically connected to the at least two leads and disposed adjacent to the anchor; and
   a spectrometer electrically connected to the at least two coil contacts, the spectrometer capable of transmitting electromagnetic radiation via the coil and of performing a Fourier analysis of the electromagnetic radiation sensed by the coil;
   wherein the probe is capable of atomic force microscopy via deflection of the beam when the tip is contacted with a sample; and
   wherein the probe, when positioned within a magnetic field, is capable of nuclear magnetic resonant spectroscopy by transmission to and reception of electromagnetic radiation from the sample via the coil.

13. The system of claim 12, wherein the magnetic field is generated by a magnet having a field strength between approximately 0 and 30 Tesla.

14. The system of claim 12, the system further comprising:
   at least one piezoelectric element mounted to the top surface of the beam at or near the proximal end, wherein the at least one piezoelectric element is capable of generating a deflection signal due to strain in the beam due to a deflection of the distal end and of moving the distal end;
   at least two piezo contacts electrically connected to the at least one piezoelectric element and disposed adjacent to the anchor; and
   a deflection circuit electrically connected to the at least two piezo contacts, the deflection circuit capable of receiving the deflection signal form the at least one piezoelectric element and of generating a movement in the at least one piezoelectric element.

15. The system of claim 12, the system further comprising:
   a data acquisition system electrically connected to the probe, the data acquisition system comprising:
      a tuning circuit electrically connected to the at least two coil contacts, the tuning circuit capable of calibrating the coil, and
      the spectrometer.

16. The system of claim 15, wherein the tuning circuit is comprised of a first capacitor electrically connected in parallel with the probe and a second capacitor electrically connected in series with the first capacitor and the probe.

17. The system of claim 12, wherein the probe is capable of identifying biophysical and biochemical characteristics of a sample contacted by the tip of the probe.

18. The device of claim 12, wherein the probe is capable of determining a morphology of the sample.

19. The device of claim 12, wherein the probe is capable of isolating intercellular structures within a cell contacted by the tip of the probe.

20. A method of using a AFM/NMR probe, the method comprising the steps of:
   placing a sample to be analyzed into a magnetic field;

introducing a probe into proximity with the sample, the probe comprising:
    a beam having a distal end, a proximal end, a top surface and a bottom surface, the beam being attached to an anchor at the proximal end and further comprising a tip extending substantially perpendicular from the bottom surface at or near the distal end, and
    a coil having at least one turn mounted to the top surface of the beam at or near the distal end opposite the tip, wherein the coil is capable of both transmitting and sensing electromagnetic radiation;
moving the probe until the tip contacts a surface of the sample, thereby ensuring close proximity between the coil and the sample;
scanning the surface with the tip by moving the tip across the surface of the sample;
while the tip is in contact with the surface of the sample, generating an electromagnetic field via the coil, the electromagnetic field being localized to the sample;
waiting a period of time for nuclei within the sample to generate a resonant signal in response to the electromagnetic field generated from the coil; and
acquiring the resonant signal generated by the nuclei within the sample via the coil.

21. The method of 20, the method further comprising the step of:
    generating the electromagnetic field via the coil and acquiring the resonant signal generated by the nuclei at multiple locations across the surface of the sample.

22. The method of 20, the method further comprising the step of:
    applying a surface chemistry to the surface of the sample, the surface chemistry selected from the group consisting of fibronectin, poly-1-lysine, and collagen.

23. The method of 21, the method further comprising the step of:
    conducting Fourier transform spectroscopy on the resonant signal generated by the nuclei using a spectrometer.

24. The method of 21, wherein the electromagnetic field generated via the coil is produced by a spectrometer and the resonant signal generated by the nuclei within the sample is acquired by the same spectrometer.

25. The method of 24, wherein the electromagnetic field generated via the coil comprises multiple pulses of electromagnetic radiation.

26. The method of 21, the method further comprising the step of:
    determining a morphology of the sample.

27. The method of 21, the method further comprising the step of:
    determining an adhesion property of the surface of the sample.

28. The method of 21, the method further comprising the step of:
    determining biophysical and biochemical characteristics of a sample contacted by the tip of the probe.

29. A method of fabricating an AFM/NMR probe, the method comprising the steps of:
    providing a beam, the beam comprising:
        a beam having a distal end, a proximal end, a top surface and a bottom surface, the beam being attached to an anchor at the proximal end and further comprising a tip extending substantially perpendicular from the bottom surface at or near the distal end;
    applying a first insulation layer of insulating material on the top surface of the beam;
    applying a first conductive layer of electrically conductive material to the first insulation layer on the beam; and
    etching the first conductive layer to define a coil at or near the distal end opposite the tip, at least one lead adjacent the coil, and at least one contact adjacent the at least one lead at or near the proximal end, wherein the coil, at least one lead, and at least one contact are electrically connected.

30. The method of claim 29, wherein the etching step is performed using a focused ion beam milling process.

31. The method of claim 29, wherein the method further comprises the steps of:
    applying a second insulation layer to the beam;
    etching the second insulation layer to form a passage to one end of the coil;
    applying a second conductive layer of electrically conductive material to the second insulation layer on the beam; and
    etching the second conductive layer to form at least one lead in electrical contact with the coil via the passage.

32. A method of fabricating the a AFM/NMR probe, the method comprising the steps of:
    forming a wafer having a top surface and a bottom surface with a first oxide layer thereon;
    etching the wafer to form an trench in the top surface;
    applying a second oxide layer within the trench;
    further etching the coated opening to form a desired tip shape;
    depositing a structural layer to the top surface and into the trench to form a beam and a tip, wherein the beam defines a top surface, a bottom surface, a distal end, and a proximal end, and wherein the tip extends substantially perpendicular from the bottom surface at or near the distal end;
    depositing a first conductive layer on the top surface over the structural layer to form a coil and at least one lead adjacent the coil, wherein the coil includes one or more ends and is disposed at or near the distal end of the beam opposite the tip, and wherein the at least one lead extends to the proximal end of the beam;
    applying an insulation layer over the first conductive layer;
    etching the first insulation layer to form one or more passages to the at least one lead and one end of the coil;
    depositing a second conductive layer over the first insulation layer to form an electrical connection between one end of the coil and at least one lead via the one or more passages;
    applying a second insulation layer over the second conductive layer;
    applying a third oxide layer over the second insulation layer;
    dissolving a portion of the wafer surrounding the tip; and
    dissolving the second oxide layer from area surrounding the tip.

* * * * *